United States Patent
Couroux et al.

(10) Patent No.: US 8,366,792 B2
(45) Date of Patent: Feb. 5, 2013

(54) DYE COMPOSITION COMPRISING A HETEROCYCLIC OXIDATION BASE AND AN INDOLE COUPLER

(75) Inventors: Anne-Marie Couroux, Saint-Ouen-d'Aunis (FR); Aziz Fadli, Chelles (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 13/389,832

(22) PCT Filed: Aug. 11, 2010

(86) PCT No.: PCT/EP2010/061707
§ 371 (c)(1),
(2), (4) Date: May 29, 2012

(87) PCT Pub. No.: WO2011/018483
PCT Pub. Date: Feb. 17, 2011

(65) Prior Publication Data
US 2012/0278997 A1 Nov. 8, 2012

Related U.S. Application Data

(60) Provisional application No. 61/234,386, filed on Aug. 17, 2009, provisional application No. 61/234,381, filed on Aug. 17, 2009, provisional application No. 61/235,110, filed on Aug. 19, 2009.

(30) Foreign Application Priority Data

Aug. 12, 2009 (FR) ...................................... 09 55637
Aug. 12, 2009 (FR) ...................................... 09 55638
Aug. 12, 2009 (FR) ...................................... 09 55640

(51) Int. Cl.
*A61Q 5/10* (2006.01)
*C07D 471/00* (2006.01)
*C07D 231/44* (2006.01)

(52) U.S. Cl. ...... 8/405; 8/570; 8/668; 8/670; 548/369.1; 546/121

(58) Field of Classification Search ............... 8/405, 570, 8/668, 670; 548/369.1; 546/121
See application file for complete search history.

(56) References Cited

U.S. PATENT DOCUMENTS

| | | | |
|---|---|---|---|
| 4,003,699 A | 1/1977 | Rose et al. | |
| RE30,199 E | 1/1980 | Rose et al. | |
| 4,823,985 A | 4/1989 | Grollier et al. | |
| 5,061,289 A | 10/1991 | Clausen et al. | |
| 5,380,340 A | 1/1995 | Neunhoeffer et al. | |
| 5,457,200 A | 10/1995 | Zimmermann et al. | |
| 5,704,948 A * | 1/1998 | Terranova et al. ............... | 8/409 |
| 5,766,576 A | 6/1998 | Lowe et al. | |
| 6,099,592 A | 8/2000 | Vidal et al. | |
| 6,338,741 B1 | 1/2002 | Vidal et al. | |
| 6,395,042 B1 | 5/2002 | Audousset | |
| 6,645,258 B2 | 11/2003 | Vidal et al. | |
| 6,730,789 B1 | 5/2004 | Birault et al. | |
| 7,285,137 B2 | 10/2007 | Vidal et al. | |
| 7,578,855 B2 | 8/2009 | Fadli | |
| 7,578,856 B2 | 8/2009 | Saunier | |
| 7,635,394 B2 | 12/2009 | Fadli et al. | |
| 7,642,360 B2 | 1/2010 | Vidal et al. | |
| 7,857,864 B2 | 12/2010 | Fadli et al. | |
| 7,918,900 B2 | 4/2011 | Cottard et al. | |

FOREIGN PATENT DOCUMENTS

| | | |
|---|---|---|
| DE | 23 59 399 A1 | 6/1975 |
| DE | 38 43 892 A1 | 6/1990 |
| DE | 41 33 957 A1 | 4/1993 |
| DE | 195 43 988 A1 | 5/1997 |
| EP | 0 770 375 A1 | 5/1997 |
| EP | 1 550 656 A1 | 7/2005 |
| EP | 1 792 606 A1 | 6/2007 |
| EP | 1 792 903 A1 | 6/2007 |
| EP | 1 870 083 A2 | 12/2007 |
| EP | 1 992 331 A1 | 11/2008 |
| FR | 2 586 913 A1 | 3/1987 |
| FR | 2 733 749 A1 | 11/1996 |
| FR | 2 801 308 A1 | 5/2001 |
| FR | 2 915 884 A1 | 11/2008 |
| FR | 2 925 309 A1 | 6/2009 |
| GB | 1 026 978 | 4/1966 |
| GB | 1 153 196 | 5/1969 |
| JP | 2-19576 | 1/1990 |
| JP | 5-163124 | 6/1993 |
| WO | WO 94/08969 | 4/1994 |
| WO | WO 94/08970 | 4/1994 |
| WO | WO 96/15765 | 5/1996 |

OTHER PUBLICATIONS

STIC Search Report dated Sep. 11, 2012.*

(Continued)

*Primary Examiner* — Eisa Elhilo
(74) *Attorney, Agent, or Firm* — O'Brien Jones, PLLC

(57) ABSTRACT

The subject of the present invention is dye composition for keratin fibers, comprising, in suitable dyeing medium, a coupler of formula (I) or addition salts thereof with an acid a particular cationic or noncationic aminopyrazolopyridine derivative. The composition of the present invention makes it possible in particular to obtain a coloring with varied, intense and/or chromatic, aesthetic and relatively nonselective shades which are highly resistant to the various attacks to which the hair may be subjected.

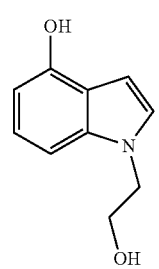

(I)

1 Claim, No Drawings

OTHER PUBLICATIONS

English language abstract for EP 0 770 375, (May 1997).
English language abstract for FR 2 915 884, (Nov. 2008).
English language abstract for FR 2 925 309, (Jun. 2009).
English language abstract for JP 2-19576, (Jan. 1990).
English language abstract for JP 5-163124, (Jun. 1993).

International Search Report for PCT/EP2010/061707, dated Nov. 18, 2010 (4 pages).
Written Opinion for PCT/EP2010/061707, dated Feb. 12, 2012 (6 pages).

* cited by examiner

DYE COMPOSITION COMPRISING A HETEROCYCLIC OXIDATION BASE AND AN INDOLE COUPLER

This is a national stage application of PCT/EP2010/061707, filed internationally on Aug. 11, 2010, which claims priority to U.S. Provisional Application No. 61/235,110, filed on Aug. 19, 2009, U.S. Provisional No. 61/234,381, filed on Aug. 17, 2009, and U.S. Provisional Application No. 61/234,386, filed on Aug. 17, 2009.

The subject of the invention is a dye composition comprising at least one heterocyclic oxidation base chosen from aminopyrazolopyridine and diaminopyrazolinone bases and a particular coupler of indole type, and also to the dyeing process using this composition.

It is known practice to dye keratin fibres, and in particular human hair, with dye compositions containing oxidation dye precursors, also generally known as oxidation bases, such as ortho- or para-phenylene-diamines, ortho- or para-aminophenols and heterocyclic compounds. These oxidation bases are colourless or weakly coloured compounds which, when combined with oxidizing products, can give rise to coloured compounds via a process of oxidative condensation.

It is also known that the shades obtained with these oxidation bases can be varied by combining them with couplers or colouring modifiers, the latter being chosen in particular from aromatic meta-diamines, meta-aminophenols, meta-diphenols and certain heterocyclic compounds such as indole compounds.

The variety of the molecules employed as oxidation bases and couplers makes it possible to obtain a rich range of colours.

The "permanent" colouring obtained by virtue of these oxidation dyes furthermore has to satisfy a certain number of requirements. Thus it must be without disadvantage toxicologically, it must make it possible to obtain shades within the desired intensity and it must behave well in the face of external agents such as light, bad weather, washing, permanent waving, perspiration and rubbing.

The dyes must also make it possible to cover white hair, and, finally, be as non-selective as possible, i.e. make it possible to obtain the smallest possible differences in colouring along the same keratin fibre, which is generally differently sensitized (i.e. damaged) between its end and its root.

It is already known practice to use aminopyrazolopyridine oxidation bases for dyeing keratin fibres, in particular in patent application FR 2801308, EP 1 792 903 or EP 1 792 606. These bases make it possible to obtain varied shades.

Document EP 1550656 describes the use of oxidation bases of the diaminopyrazolinone type for dyeing keratin fibres, in particular the hair.

However, these bases are not always satisfactory in terms of intensity, of chromaticity, of selectivity and of resistance, in particular to shampooing.

The aim of the present invention is to obtain a composition for dyeing the hair which has improved dyeing properties, in particular in terms of intensity or of chromaticity, and/or of selectivity and/or of resistance to external agents.

A subject of the present invention is therefore a dye composition for keratin fibres, comprising, in a suitable dyeing medium, a coupler of formula (I) or addition salts thereof with an acid

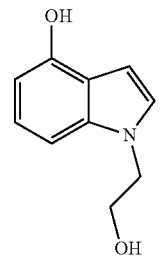

(I)

one or more heterocyclic oxidation bases chosen from the aminopyrazolopyridine bases of formula (II) or (III) and the diamino-N,N-dihydropyrazolone bases of formula (IV)

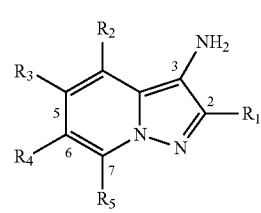

(II)

in which:
$R_1$, $R_2$, $R_3$, $R_4$ and $R_5$, which may be identical or different, represent a hydrogen or halogen atom; an —$NHSO_3H$ radical; a hydroxyl radical; a ($C_1$-$C_4$)alkyl radical; a ($C_1$-$C_4$)alkoxy radical; a ($C_1$-$C_4$)alkylthio radical; mono ($C_1$-$C_4$)alkylamino; a di($C_1$-$C_4$)alkylamino radical in which the two alkyl groups can, together with the nitrogen atom to which they are attached, form a ring which can be interrupted with one or more nitrogen, oxygen or sulphur atoms; a heterocycle; a nitro radical; a phenyl radical; a carbonyl radical; a ($C_1$-$C_4$)alkoxycarbonyl radical; a carboxamido radical; a cyano radical; an amino radical; a sulphonyl radical; a —$CO_2H$ radical, an —$SO_3H$ radical; a —$PO_3H_2$ radical; a —$PO_4H_2$ radical; or a group:

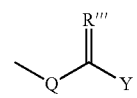

in which R''' represents an oxygen or nitrogen atom, Q represents an oxygen atom, an NH group or an NH($C_1$-$C_4$)alkyl group, and Y represents a hydroxyl, amino, $C_1$-$C_4$ alkyl, ($C_1$-$C_4$)alkoxy, ($C_1$-$C_4$)alkylamino, or di($C_1$-$C_4$)alkylamino radical; or

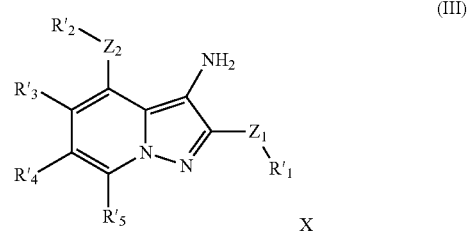

(III)

in which:

$Z_1$ and $Z_2$ independently represent
- a single covalent bond,
- a divalent radical chosen from:
  - an —O(CH$_2$)$_p$— radical, p denoting an integer ranging from 0 to 6,
  - an —NR'$_6$(CH$_2$)$_q$(C$_6$H$_4$)$_t$— radical, q denoting an integer ranging from 0 to 6 and t denoting 0 or 1. R'$_6$ represents a hydrogen atom or a C$_1$-C$_6$ alkyl radical optionally substituted with one or more hydroxyl groups, $Z_1$ can also represent a divalent radical —S—, —SO— or —SO$_2$— when R'$_1$ is a methyl radical, R'$_1$ and R'$_2$ represent independently:
- a hydrogen,
- a C$_1$-C$_{10}$ alkyl radical, which is optionally substituted and optionally interrupted with a heteroatom or a group chosen from O, N, Si, S, SO and SO$_2$,
- a halogen,
- an SO$_3$H radical,
- a saturated, unsaturated or aromatic, substituted or unsubstituted, 5- to 8-membered ring optionally containing one or more heteroatoms or groups chosen from N, O, S, SO$_2$ and —CO—, it being possible for the ring to be cationic and/or substituted with a cationic radical,
- an —N$^+$R$_{17}$R$_{18}$R$_{19}$ group, R$_{17}$, R$_{18}$, and R$_{19}$ being linear or branched C$_1$-C$_5$ alkyls optionally substituted with one or more hydroxyl groups, when $Z_1$ or $Z_2$ represents a covalent bond, then R'$_1$ or R'$_2$ can also represent one of the following radicals:
- optionally substituted C$_1$-C$_6$ alkylcarbonyl,
- —O—CO—R, —CO—O—R, NR—CO—R' or —CO—NRR' in which R and R' independently represent a hydrogen atom or an optionally substituted C$_1$-C$_6$ alkyl radical, R'$_3$, R'$_4$ and R'$_5$, which may be identical or different, represent:
- a hydrogen atom,
- a hydroxyl radical,
- a C$_1$-C$_6$ alkoxy radical,
- a C$_1$-C$_6$ alkylthio radical,
- an amino radical,
- a monoalkylamino radical,
- a C$_1$-C$_6$ dialkylamino radical in which the alkyl radicals can form, with the nitrogen atom to which they are attached, a saturated or unsaturated and aromatic or non-aromatic 5- to 8-membered heterocycle which can contain one or more heteroatoms or groups chosen from N, O, S, SO$_2$ and CO, it being possible for the heterocycle to be cationic and/or substituted with a cationic radical,
- an optionally substituted C$_1$-C$_6$ alkylcarbonyl radical,
- an —O—CO—R, —CO—O—R, NR—CO—R' or —CO—NRR' radical with R and R' as defined above,
- a halogen,
- an —NHSO$_3$H radical,
- an optionally substituted C$_1$-C$_4$ alkyl radical,
- a saturated, unsaturated or aromatic and optionally substituted carbon ring,
- it being possible for R'$_3$, R'$_4$ and R'$_5$ to form, in pairs, a partially saturated or unsaturated ring, X represents an ion or a group of ions which makes it possible to provide the electronegativity of the derivative of formula (III), with the condition that at least one of the groups R'$_1$ and R'$_2$ represents a cationic radical,

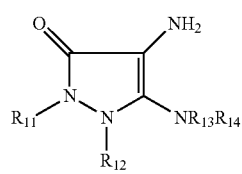

in which:

$R_{11}$, $R_{12}$, $R_{13}$ and $R_{14}$, which may be identical or different, represent:
- a linear or branched C$_1$-C$_6$ alkyl radical optionally substituted with one or more radicals chosen from the group constituted of an OR$_{15}$ radical, an NR$_6$R$_7$ radical, a carboxyl radical, a sulphonic radical, a carboxamido radical CONR$_{16}$R$_{17}$, a sulphonamido radical SO$_2$NR$_{16}$R$_{17}$, a heteroaryl, an aryl optionally substituted with a (C$_1$-C$_4$) alkyl group, a hydroxyl, a C$_1$-C$_2$ alkoxy, an amino, a (di)(C$_1$-C$_2$)alkylamino;
- an aryl radical optionally substituted with one or more (C$_1$-C$_4$)alkyl, hydroxyl, C$_1$-C$_2$ alkoxy, amino, (di)(C$_1$-C$_2$)alkylamino;
- a 5- or 6-membered heteroaryl radical optionally substituted with one or more radicals chosen from (C$_1$-C$_4$) alkyl and (C$_1$-C$_2$)alkoxy;

$R_{13}$ and $R_{14}$ can also represent a hydrogen atom;

$R_{15}$, $R_{16}$ and $R_{17}$, which may be identical or different, represent a hydrogen atom; a linear or branched C$_1$-C$_4$ alkyl radical optionally substituted with one or more radicals chosen from the group constituted of a hydroxyl, a C$_1$-C$_2$ alkoxy, a carboxamido CONR$_{18}$R$_{19}$, a sulphonyl SO$_2$R$_{18}$, an aryl optionally substituted with a (C$_1$-C$_4$)alkyl, a hydroxyl, a C$_1$-C$_2$ alkoxy, an amino, a (di)(C$_1$-C$_2$)alkylamino; an aryl optionally substituted with a (C$_1$-C$_4$)alkyl, a hydroxyl, a C$_1$-C$_2$ alkoxy, an amino, a (di)(C$_1$-C$_2$)alkylamino;

$R_{16}$ and $R_{17}$, which may be identical or different, can also represent a carboxamido radical CONR$_{18}$R$_{19}$; a sulphonyl SO$_2$R$_{18}$;

$R_{18}$ and $R_{19}$, which may be identical or different, represent a hydrogen atom; a linear or branched C$_1$-C$_4$ alkyl radical optionally substituted with one or more hydroxyl or C$_1$-C$_2$ alkoxy;

$R_{11}$ and $R_{12}$, on the one hand, and $R_{13}$ and $R_{14}$, on the other hand, can form, with the nitrogen atoms to which they are attached, a saturated or unsaturated heterocycle comprising 5 to 7 ring members, optionally substituted with one or more radicals chosen from the group constituted of halogen atoms, amino, (di)(C$_1$-C$_4$)alkylamino, hydroxyl, carboxyl, carboxamido and (C$_1$-C$_2$)alkoxy radicals, and C$_1$-C$_4$ alkyl radicals optionally substituted with one or more hydroxyl, amino, (di)alkylamino, alkoxy, carboxyl or sulphonyl radicals;

$R_{13}$ and $R_{14}$ can also form, together with the nitrogen atom to which they are attached, a 5- or 7-membered heterocycle, the carbon atoms of which can be replaced with an optionally substituted oxygen or nitrogen atom.

The present invention makes it possible in particular to obtain intense or chromatic shades which are relatively non-selective and resistant to shampooing.

Another subject of the invention is a process for dyeing keratin fibres using the composition of the present invention, and also the use of this composition for dyeing keratin fibres.

In the compounds of formulae (II) to (IV) above, and unless otherwise indicated, the expression "alkyl" used for the alkyl radicals and for the groups comprising an alkyl part means a linear or branched carbon chain containing from 1 to 4 carbon atoms, which is substituted or unsubstituted with one or more heterocycles or with one or more phenyl groups or with one or more groups chosen from halogen atoms, such as chlorine, bromine, iodine and fluorine, or hydroxyl, alkoxy, amino, carbonyl, carboxamido, sulphonyl, —$CO_2H$, —$SO_3H$, —$PO_3H_2$, $PO_4H_2$, —$NHSO_3H$, sulphonamide, mono($C_1$-$C_4$) alkylamino or tri($C_1$-$C_4$)alkylammonium radicals, or else with a di($C_1$-$C_4$)alkylamino radical in which the two alkyl groups can form, together with the nitrogen atom of said di($C_1$-$C_4$)alkylamino group to which they are attached, a ring which can be interrupted with one or more nitrogen, oxygen or sulphur atoms.

Likewise, according to the invention, the expression "alkoxy" used for the alkoxy radicals and for the groups comprising an alkoxy part means a linear or branched O-carbon chain containing from 1 to 4 carbon atoms, which is unsubstituted or substituted with one or more groups chosen from heterocycles; halogen atoms, such as chlorine, bromine, iodine and fluorine; or hydroxyl, amino, carbonyl, carboxamido, sulphonyl, —$CO_2H$, —$SO_3H$, —$PO_3H_2$—$PO_4H_2$, —$NHSO_3H$, sulphonamide, mono($C_1$-$C_4$)alkylamino, or tri ($C_1$-$C_4$)alkylammonium radicals, or else with a di($C_1$-$C_4$) alkylamino radical in which the two alkyl groups can form, together with the nitrogen atom of said di($C_1$-$C_4$)alkylamino group to which they are attached, a ring which can be interrupted with one or more nitrogen, oxygen or sulphur atoms.

According to the invention, the term "heterocycle" is understood to mean a 5-, 6-, 7- or 8-membered aromatic or non-aromatic ring comprising from 1 to 3 heteroatoms chosen from nitrogen, sulphur and oxygen atoms. These heterocycles can be fused to other heterocycles or to a phenyl group. They can be substituted with a halogen atom; a ($C_1$-$C_4$)alkyl radical; a ($C_1$-$C_4$)alkoxy radical; a hydroxyl radical; an amino radical; a ($C_1$-$C_4$)alkylamino radical; or a di($C_1$-$C_4$)alkylamino radical in which the two alkyl groups can, together with the nitrogen atom to which they attached, form a ring which can be interrupted with one or more nitrogen, oxygen or sulphur atoms. These heterocycles can in addition be quaternized with a ($C_1$-$C_4$)alkyl radical.

Among these optionally fused heterocycles, mention may in particular be made, by way of example, of the following rings: thiadiazole, triazole, isoxazole, oxazole, azaphosphole, triazole, isothiazole, imidazole, pyrazole, triazine, triazine, pyrazine, pyridazine, pyrimidine, pyridine, diazepine, oxazepine, benzotriazole, benzoxazole, benzimidazole, benzothiazole, morpholine, piperidine, piperazine, azetidine, pyrrolidine, aziridine, 3-(2-hydroxyethyl)benzothiazol-3-ium and 1-(2-hydroxy-ethyl)pyridinium.

According to the invention, the term "phenyl" is understood to mean a phenyl radical which is unsubstituted or substituted with one or more cyano, carbonyl, carboxamido, sulphonyl, —$CO_2H$, —$SO_3H$, —$PO_3H_2$, —$PO_4H_2$, hydroxyl, amino, mono($C_1$-$C_4$)alkylamino or di($C_1$-$C_4$)alkylamino radicals, it being possible, in the case of the last radical, for the two alkyl groups to form, together with the nitrogen atom of said di($C_1$-$C_4$)alkylamino group to which they are attached, a ring which can be interrupted with one or more nitrogen, oxygen or sulphur atoms.

Among the

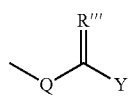

groups, mention may in particular be made of acetamide, dimethylurea, O-methylcarbamate, methyl carbonate and N-dimethylcarbonate groups, and esters.

Among the compounds of formula (II) above, preference is given to the 3-aminopyrazolo[1,5-a]pyridines corresponding to the following subformula, and addition salts thereof with an acid or with a base:

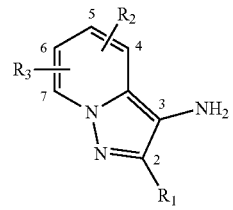

in which:
$R_1$, $R_2$ and $R_3$, which may be identical or different, represent a hydrogen or halogen atom; a hydroxyl radical; a ($C_1$-$C_4$) alkyl radical; a ($C_1$-$C_4$)alkylthio radical; a ($C_1$-$C_4$)alkoxy radical; an —$NHSO_3H$ radical; an amino radical; a ($C_1$-$C_4$) alkylamino radical; a di($C_1$-$C_4$)alkylamino radical in which the two alkyl groups can, together with the nitrogen atom to which they are attached, form a ring which can be interrupted with one or more nitrogen, oxygen or sulphur atoms; a heterocycle as defined above; a sulphonamide radical; a carbonyl radical; a ($C_1$-$C_4$)alkoxycarbonyl radical, a carboxamido radical, or a group of formula:

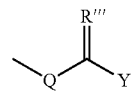

in which R''' represents an oxygen or nitrogen atom, Q represents an oxygen atom, an NH group or an NH($C_1$-$C_4$)alkyl group, and Y represents a hydroxyl, amino, $C_1$-$C_4$ alkyl, ($C_1$-$C_4$)alkoxy, ($C_1$-$C_4$)alkylamino or di($C_1$-$C_4$)alkylamino radical.

Among the 3-aminopyrazolo[1,5-a]pyridines of formula (II) which can be used as oxidation base in the dye compositions in accordance with the invention, mention may in particular be made of:
pyrazolo[1,5-a]pyridin-3-ylamine;
2-acetylaminopyrazolo[1,5-a]pyridin-3-ylamine;
2-morpholin-4-ylpyrazolo[1,5-a]pyridin-3-ylamine;
3-aminopyrazolo[1,5-a]pyridine-2-carboxylic acid;
2-methoxypyrazolo[1,5-a]pyridin-3-ylamino;
(3-aminopyrazolo[1,5-a]pyridin-7-yl)methanol;
2-(3-aminopyrazolo[1,5-a]pyridin-5-yl)ethanol;
2-(3-aminopyrazolo[1,5-a]pyridin-7-yl)ethanol;
(3-aminopyrazolo[1,5-a]pyridin-2-yl)methanol;
3,6-diaminopyrazolo[1,5-a]pyridine;
3,4-diaminopyrazolo[1,5-a]pyridine;
pyrazolo[1,5-a]pyridine-3,7-diamine;
7-morpholin-4-ylpyrazolo[1,5-a]pyridin-3-ylamine;
pyrazolo[1,5-a]pyridine-3,5-diamine;
5-morpholin-4-ylpyrazolo[1,5-a]pyridin-3-ylamine;
2-[(3-aminopyrazolo[1,5-a]pyridin-5-yl)(2-hydroxyethyl) amino]ethanol;
2-[(3-aminopyrazolo[1,5-a]pyridin-7-yl)(2-hydroxyethyl) amino]ethanol;
3-aminopyrazolo[1,5-a]pyridin-5-ol;

3-aminopyrazolo[1,5-a]pyridin-4-ol;
3-aminopyrazolo[1,5-a]pyridin-6-ol;
3-aminopyrazolo[1,5-a]pyridin-7-ol;
2-methoxy-6,7-dimethylpyrazolo[1,5-a]pyridin-3-amine;
2-[(3-aminopyrazolo[1,5-a]pyridin-2-yl)oxy]ethanol;
4-ethyl-2-methoxy-7-methylpyrazolo[1,5-a]pyridin-3-amine hydrochloride;
1-(3-aminopyrazolo[1,5-a]pyridin-2-yl)pyrrolidin-3-ol;
2,2'-[(3-aminopyrazolo[1,5-a]pyridin-2-yl)imino]diethanol;
2-[(3-aminopyrazolo[1,5-a]pyridin-2-yl)amino]ethanol;
N2-(2-pyridin-3-ylethyl)pyrazolo[1,5-a]pyridine-2,3-diamine;
and addition salts thereof with an acid or with a base.

Among the bases described above, 2-[(3-aminopyrazolo[1,5-a]pyridin-2-yl)oxy]ethanol and addition salts thereof with an acid are particularly preferred.

The vast majority of the 3-aminopyrazolo[1,5-a]pyridines of formula (II) are compounds which are known in the pharmaceutical field and are described in particular in U.S. Pat. No. 5,457,200. These compounds can be prepared according to methods of synthesis that are well known in the literature and as described, for example, in U.S. Pat. No. 5,457,200.

The term "cationic ring" or "cationic heterocycle" is understood to mean a ring containing one or more quaternary ammonium groups.

By way of example of radicals of the —$N^+R_{17}R_{18}R_{19}$ type, mention may be made of trimethylammonium, triethylammonium, dimethylethylammonium, diethylmethyl-ammonium, diisopropylmethylammonium, diethylpropyl-ammonium, β-(hydroxyethyl)diethylammonium, di(β-hydroxyethyl)methylammonium or tri(β-hydroxy-ethyl) ammonium radicals.

By way of example of cationic heterocycles, mention may be made of imidazolium, pyridinium, piperazinium, pyrrolidinium, morpholinium, pyrimidinium, triazolium, benzimidazolium, benzothiazolium, oxazolium, benzotriazolium, pyrazolium, triazolium or benzoxazolium heterocycles.

By way of example of cationic heterocycles, mention may be made of imidazoliums, pyridiniums, piperaziniums, pyrrolidiniums, morpholiniums, pyrimidiniums, triazoliums, benzimidazoliums, benzothiazoliums, oxazoliums, benzotriazoliums, pyrazoliums, triazoliums or benzoxazoliums.

The compounds of formula (III) can optionally be salified with strong inorganic acids such as, for example, HCl, HBr, HI, $H_2SO_4$ or $H_3PO_4$, or organic acids such as, for example, acetic acid, lactic acid, tartaric acid, citric acid, succinic acid, benzenesulphonic acid, para-toluenesulphonic acid, formic acid or methanesulphonic acid.

If they have anionic groups such as —$CO_2H$, —$SO_3H$, —$PO_3H_2$ or —$PO_4H_2$ groups, the compounds of formula (II) can be salified with alkali metal or alkaline earth metal hydroxides, such as sodium hydroxide or potassium hydroxide, with aqueous ammonia or with organic amines.

They can also be in the form of solvates, for example a hydrate or a solvate of a linear or branched alcohol, such as ethanol or isopropanol.

In the context of the invention, the term "derivative of formula (III)" is understood to mean all mesomeric or isomeric forms.

By way of examples of derivatives of the formula (III), mention may be made of the following compounds in which $X^-$ is as defined above:

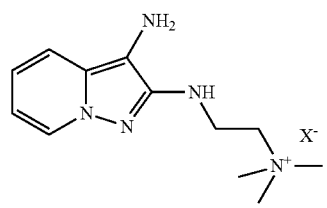

Salt of [2-(3-aminopyrazolo[1,5-a]pyridin-2-yl-amino)ethyl]trimethylammonium

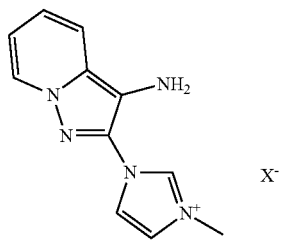 [SMILES: C[n+]1ccn(-c2nn3ccccc3c2N)c1 ; "X-"]

Salt of 3-(3-aminopyrazolo[1,5-a]pyridin-2-yl)-1-methyl-3H-imidazol-1-ium

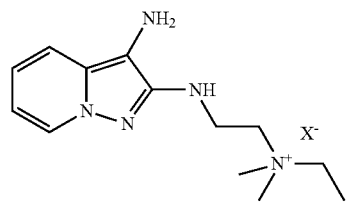

Salt of [2-(3-aminopyrazolo[1,5-a]pyridin-2-ylamino)ethyl]ethyldimethylammonium

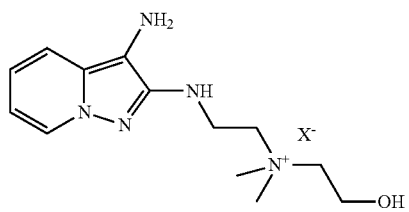 Salt of [2-(3-aminopyrazolo[1,5-a]pyridin-2-ylamino)ethyl](2-hydroxyethyl)dimethylammonium

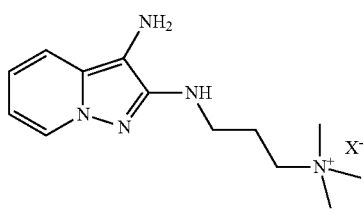 Salt of [3-(3-aminopyrazolo[1,5-a]pyridin-2-ylamino)propyl]trimethylammonium

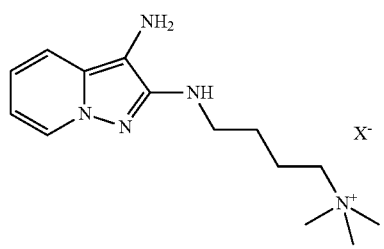 Salt of [4-(3-aminopyrazolo[1,5-a]pyridin-2-ylamino)butyl]trimethylammonium

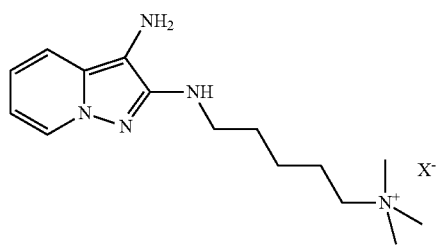 Salt of [5-(3-aminopyrazolo[1,5-a]pyridin-2-ylamino)pentyl]trimethylammonium

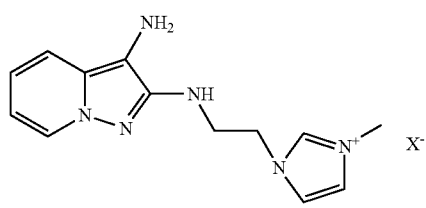 Salt of 3-[2-(3-aminopyrazolo[1,5-a]pyridin-2-ylamino)ethyl]-1-methyl-3H-imidazol-1-ium

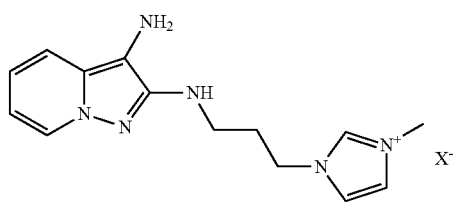 Salt of 3-[3-(3-aminopyrazolo[1,5-a]pyridin-2-ylamino)propyl]-1-methyl-3H-imidazol-1-ium

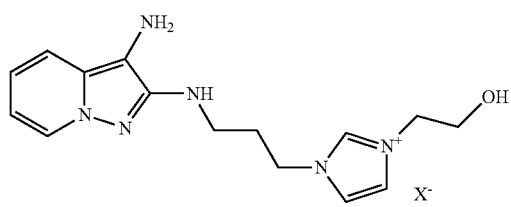 Salt of 3-[3-(3-aminopyrazolo[1,5-a]pyridin-2-ylamino)propyl]-1-(2-hydroxyethyl)-3H-imidazol-1-ium

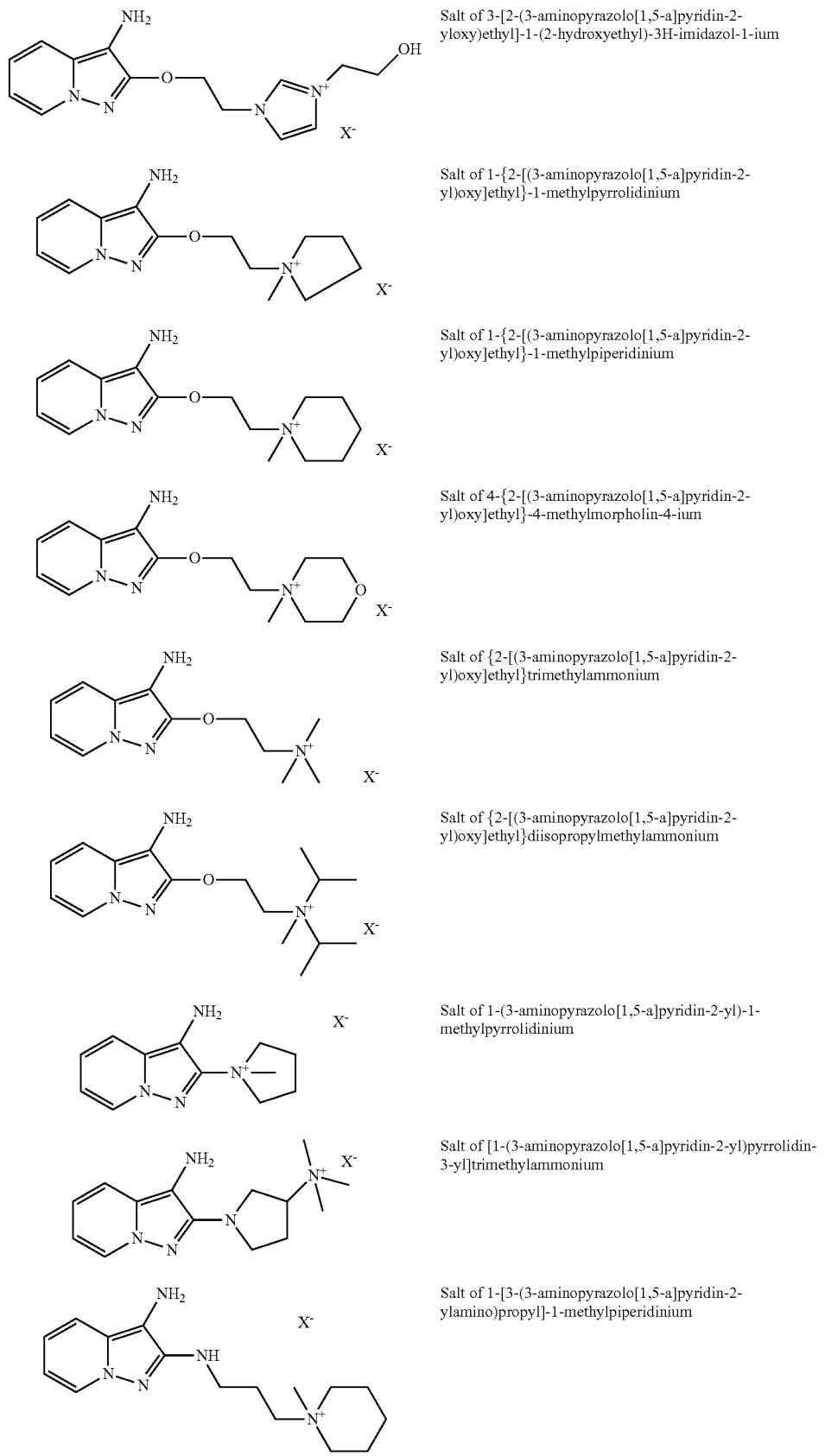

| | |
|---|---|
| | Salt of 3-[2-(3-aminopyrazolo[1,5-a]pyridin-2-yloxy)ethyl]-1-(2-hydroxyethyl)-3H-imidazol-1-ium |
| | Salt of 1-{2-[(3-aminopyrazolo[1,5-a]pyridin-2-yl)oxy]ethyl}-1-methylpyrrolidinium |
| | Salt of 1-{2-[(3-aminopyrazolo[1,5-a]pyridin-2-yl)oxy]ethyl}-1-methylpiperidinium |
| | Salt of 4-{2-[(3-aminopyrazolo[1,5-a]pyridin-2-yl)oxy]ethyl}-4-methylmorpholin-4-ium |
| | Salt of {2-[(3-aminopyrazolo[1,5-a]pyridin-2-yl)oxy]ethyl}trimethylammonium |
| | Salt of {2-[(3-aminopyrazolo[1,5-a]pyridin-2-yl)oxy]ethyl}diisopropylmethylammonium |
| | Salt of 1-(3-aminopyrazolo[1,5-a]pyridin-2-yl)-1-methylpyrrolidinium |
| | Salt of [1-(3-aminopyrazolo[1,5-a]pyridin-2-yl)pyrrolidin-3-yl]trimethylammonium |
| | Salt of 1-[3-(3-aminopyrazolo[1,5-a]pyridin-2-ylamino)propyl]-1-methylpiperidinium |

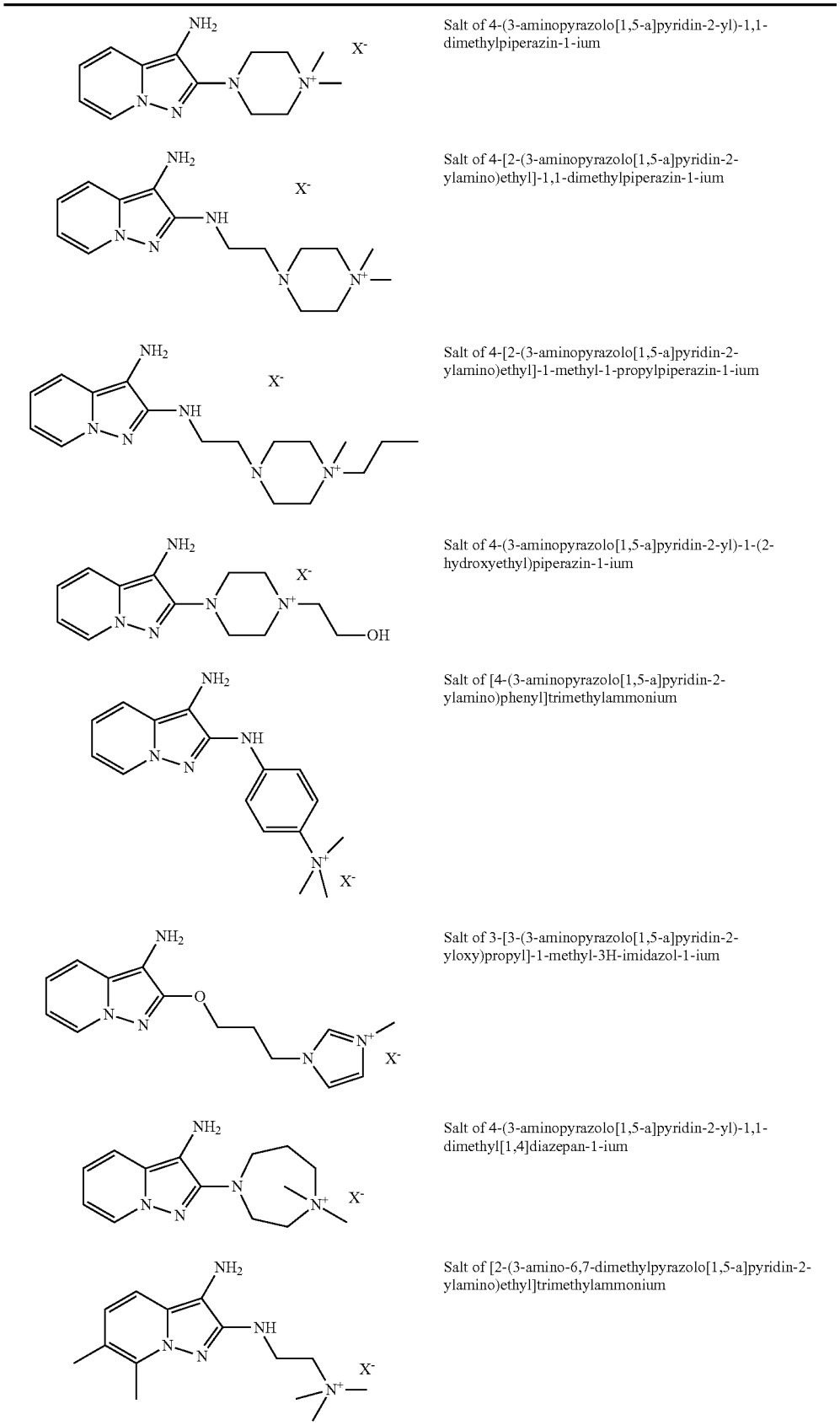

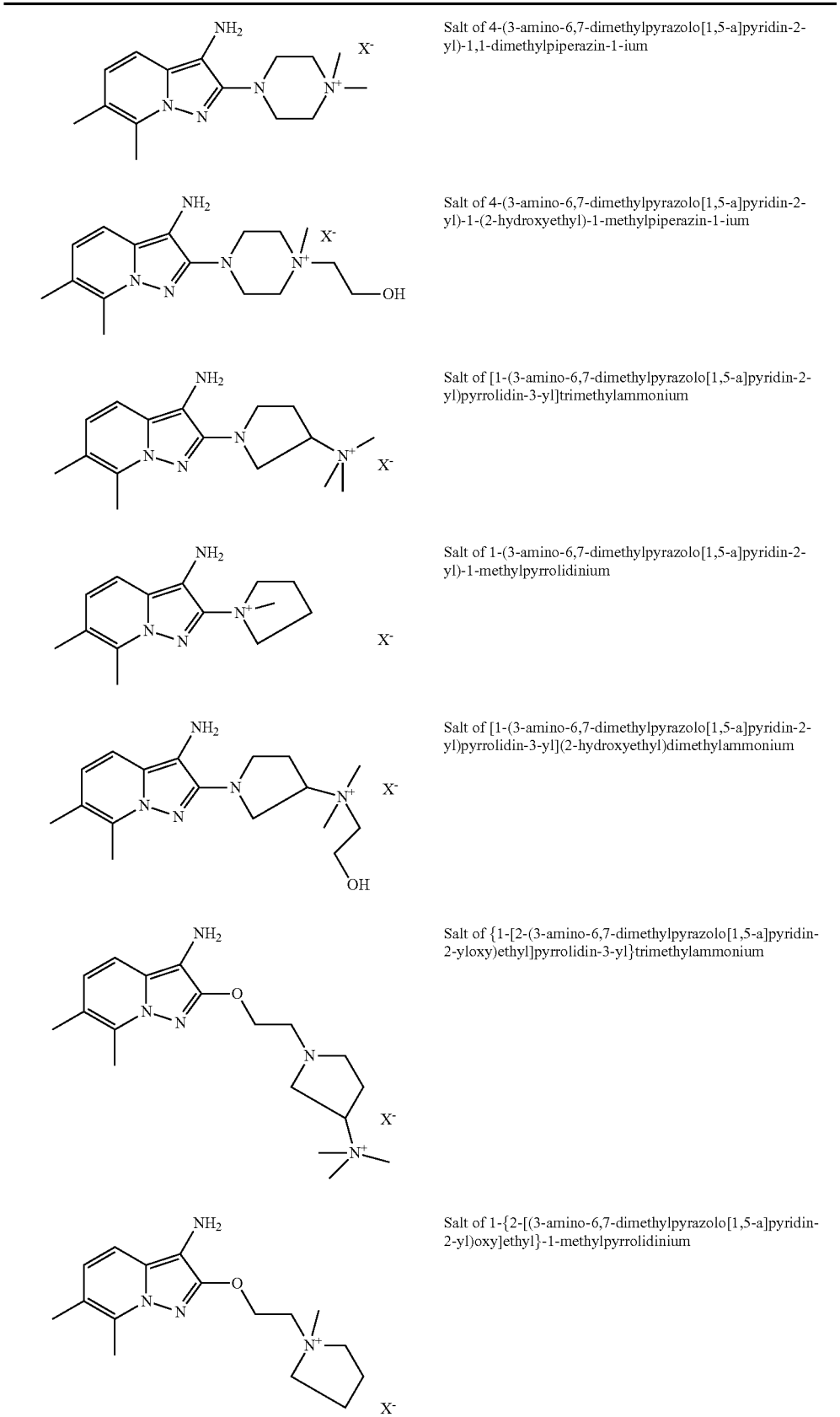

Salt of 4-(3-amino-6,7-dimethylpyrazolo[1,5-a]pyridin-2-yl)-1,1-dimethylpiperazin-1-ium Salt of 4-(3-amino-6,7-dimethylpyrazolo[1,5-a]pyridin-2-yl)-1-(2-hydroxyethyl)-1-methylpiperazin-1-ium Salt of [1-(3-amino-6,7-dimethylpyrazolo[1,5-a]pyridin-2-yl)pyrrolidin-3-yl]trimethylammonium Salt of 1-(3-amino-6,7-dimethylpyrazolo[1,5-a]pyridin-2-yl)-1-methylpyrrolidinium Salt of [1-(3-amino-6,7-dimethylpyrazolo[1,5-a]pyridin-2-yl)pyrrolidin-3-yl](2-hydroxyethyl)dimethylammonium Salt of {1-[2-(3-amino-6,7-dimethylpyrazolo[1,5-a]pyridin-2-yloxy)ethyl]pyrrolidin-3-yl}trimethylammonium Salt of 1-{2-[(3-amino-6,7-dimethylpyrazolo[1,5-a]pyridin-2-yl)oxy]ethyl}-1-methylpyrrolidinium

| | |
|---|---|
| 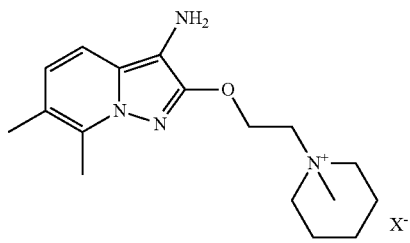 | Salt of 1-{2-[(3-amino-6,7-dimethylpyrazolo[1,5-a]pyridin-2-yl)oxy]ethyl}-1-methylpiperidinium |
| 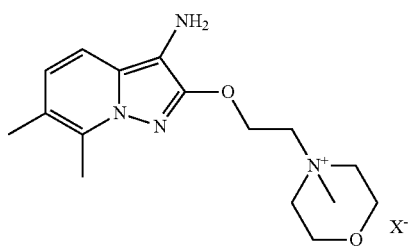 | Salt of 4-{2-[(3-amino-6,7-dimethylpyrazolo[1,5-a]pyridin-2-yl)oxy]ethyl}-4-methylmorpholin-4-ium |
| 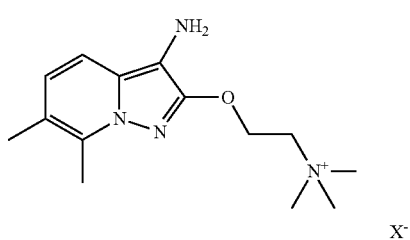 | Salt of {2-[(3-amino-6,7-dimethylpyrazolo[1,5-a]pyridin-2-yl)oxy]ethyl}trimethylammonium |
| 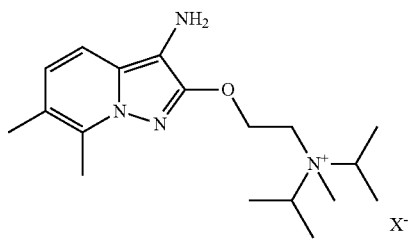 | Salt of {2-[(3-amino-6,7-dimethylpyrazolo[1,5-a]pyridin-2-yl)oxy]ethyl}diisopropylmethylammonium |
| 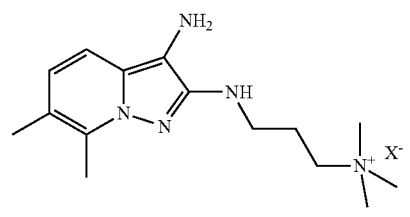 | Salt of [3-(3-amino-6,7-dimethylpyrazolo[1,5-a]pyridin-2-ylamino)propyl]trimethylammonium |
| 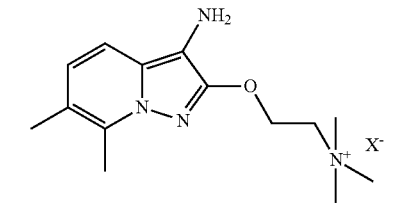 | Salt of [3-(3-amino-6,7-dimethylpyrazolo[1,5-a]pyridin-2-yloxy)propyl]trimethylammonium |
| 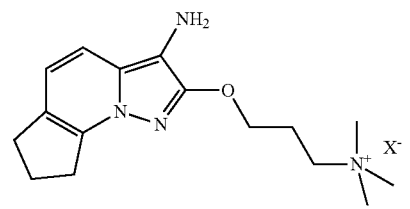 | Salt of [3-(3-amino-7,8-dihydro-6H-cyclopenta[e]pyrazolo[1,5-a]pyridin-2-yloxy)propyl]trimethylammonium |

-continued

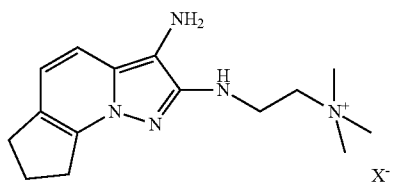
Salt of {2-[(3-amino-7,8-dihydro-6H-cyclopenta[e]pyrazolo[1,5-a]pyridin-2-yl)amino]ethyl}trimethylammonium

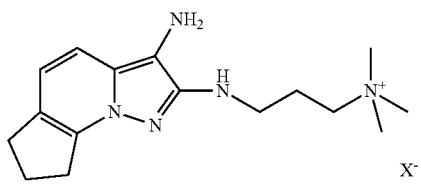
Salt of {3-[(3-amino-7,8-dihydro-6H-cyclopenta[e]pyrazolo[1,5-a]pyridin-2-yl)amino]propyl}trimethylammonium

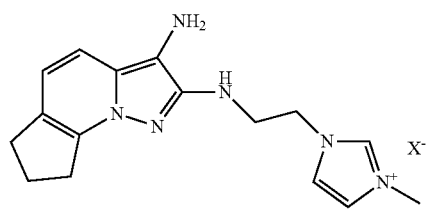
Salt of 1-{2-[(3-amino-7,8-dihydro-6H-cyclopenta[e]pyrazolo[1,5-a]pyridin-2-yl)amino]ethyl}-3-methyl-1H-imidazol-3-ium

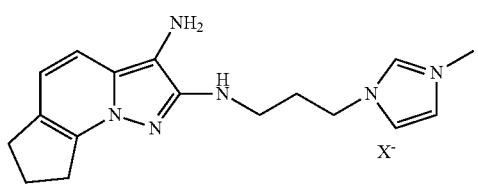
Salt of 1-{3-[(3-amino-7,8-dihydro-6H-cyclopenta[e]pyrazolo[1,5-a]pyridin-2-yl)amino]propyl}-3-methyl-1H-imidazol-3-ium

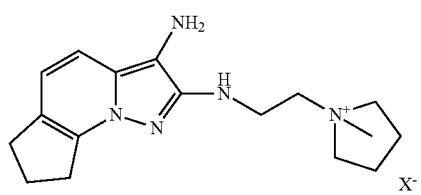
Salt of 1-{2-[(3-amino-7,8-dihydro-6H-cyclopenta[e]pyrazolo[1,5-a]pyridin-2-yl)amino]ethyl}-1-methylpyrrolidinium

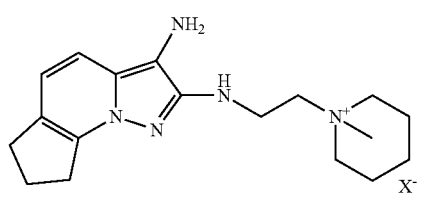
Salt of 1-{2-[(3-amino-7,8-dihydro-6H-cyclopenta[e]pyrazolo[1,5-a]pyridin-2-yl)amino]ethyl}-1-methylpiperidinium

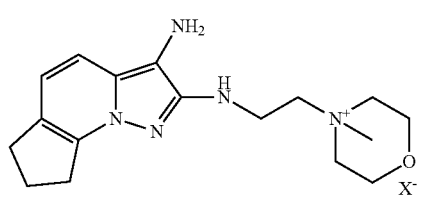
Salt of 4-{2-[(3-amino-7,8-dihydro-6H-cyclopenta[e]pyrazolo[1,5-a]pyridin-2-yl)amino]ethyl}-4-methylmorpholin-4-ium

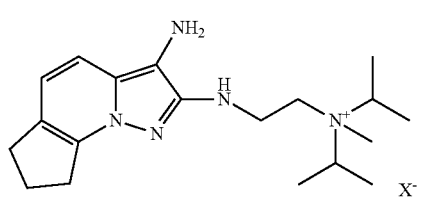
Salt of {2-[(3-amino-7,8-dihydro-6H-cyclopenta[e]pyrazolo[1,5-a]pyridin-2-yl)amino]ethyl}diisopropylmethylammonium

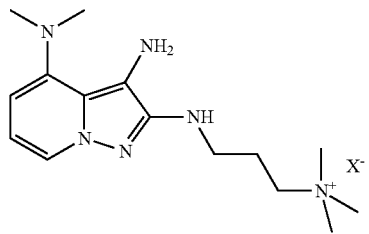
Salt of [3-(3-amino-4-dimethylaminopyrazolo[1,5-a]pyridin-2-ylamino)propyl]trimethylammonium

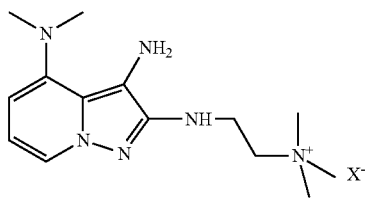
Salt of [2-(3-amino-4-dimethylaminopyrazolo[1,5-a]pyridin-2-ylamino)ethyl]trimethylammonium

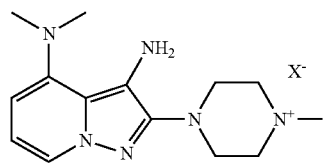
Salt of 4-(3-amino-4-dimethylaminopyrazolo[1,5-a]pyridin-2-yl)-1-methylpiperazin-1-ium

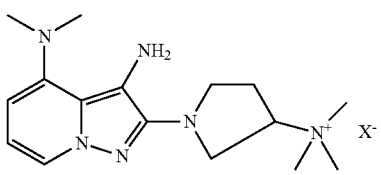
Salt of [1-(3-amino-4-dimethylaminopyrazolo[1,5-a]pyridin-2-yl)pyrrolidin-3-yl]trimethylammonium

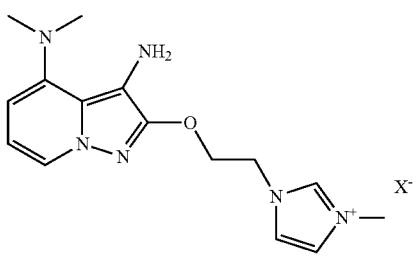
Salt of 3-[2-(3-amino-4-dimethylaminopyrazolo[1,5-a]pyridin-2-yloxy)ethyl]-1-methyl-3H-imidazol-1-ium

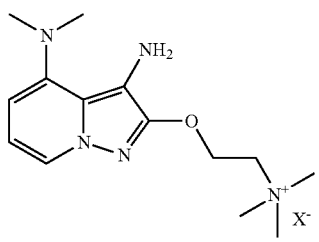
Salt of [2-(3-amino-4-dimethylaminopyrazolo[1,5-a]pyridin-2-yloxy)ethyl]trimethylammonium

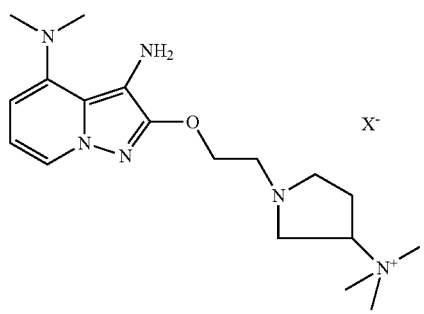 [SMILES: CN(C)c1cccn2nc(OCCN3CCC([N+](C)(C)C)C3)c(N)c12 ; "X-"]
Salt of {1-[2-(3-amino-4-dimethylaminopyrazolo[1,5-a]pyridin-2-yloxy)ethyl]pyrrolidin-3-yl}trimethylammonium -continued

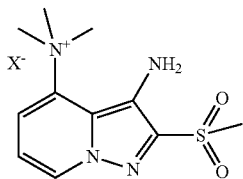

Salt of (3-amino-2-methanesulphonylpyrazolo[1,5-a]pyridin-4-yl)trimethylammonium

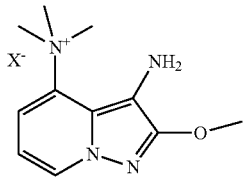

Salt of (3-amino-2-methoxypyrazolo[1,5-a]pyridin-4-yl) trimethylammonium

The nature of the counterion is not determining with regard to the dyeing power of the compounds of formula (III).

When $R'_1$ or $R'_2$ denotes a heterocycle, this heterocycle is preferably a cationic heterocycle or a heterocycle substituted with a cationic radical. By way of example, mention may be made of imidazoles substituted with a quaternary ammonium radical or imidazoliums, piperazines substituted with a quaternary ammonium radical or piperaziniums, pyrrolidines substituted with a quaternary ammonium radical or pyrrolidiniums, and diazepanes substituted with a quaternary ammonium radical or diazepaniums.

According to a different embodiment, $R'_1$ or $R'_2$ represents an $-N^+R_{17}R_{18}R_{19}$ radical, $R_{17}$, $R_{18}$ and $R_{19}$ being linear or branched $C_1$-$C_5$ alkyls optionally substituted with one or more hydroxyl groups, such as trialkylammonium, tri(hydroxyalkyl)ammonium, (hydroxyalkyl)dialkylammonium or di(hydroxyalkyl)alkylammonium.

The $R'_3$, $R'_4$ and $R'_5$ radicals can independently be a hydrogen atom or an optionally substituted $C_1$-$C_4$ alkyl radical. By way of example, mention may be made of methyl, ethyl, hydroxyethyl, aminoethyl, propyl or butyl radicals. According to one particular embodiment, $R'_3$, $R'_4$ and $R'_5$ independently represent a hydrogen atom or a $C_1$-$C_4$ alkyl radical.

According to one particular embodiment, $R'_4$ and $R'_5$ together form a partially saturated or unsaturated 5- or 8-membered ring, in particular a cyclopentene or a cyclohexene, which is optionally substituted.

According to one particular embodiment, the compound of formula (III) corresponds to the following formula (III'):

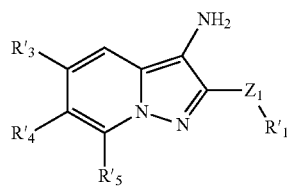

in which $Z_1$, $R'_1$, $R'_3$, $R'_4$ and $R'_5$ are as defined above.

According to one particular embodiment of this formula, $Z_1$ represents a covalent bond, an $-NR'_6(CH_2)_q-$ radical or an $-O(CH_2)_p-$ radical and $R'_1$ is a cationic radical.

By way of cationic oxidation bases of formula (III), those most particularly preferred are the following bases:

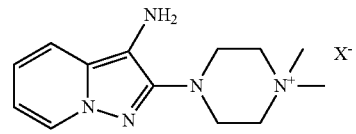

Salt of 4-(3-aminopyrazolo[1,5-a]pyridin-2-yl)-1,1-dimethylpiperazin-1-ium

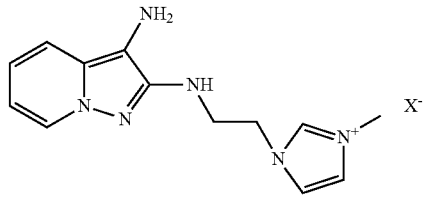

Salt of 3-[2-(3-aminopyrazolo[1,5-a]pyridin-2-ylamino)ethyl]-1-methyl-3H-imidazol-1-ium More particularly, in formula (IV), the $R_{11}$ and $R_{12}$ radicals, which may be identical or different, are chosen from:
a $C_1$-$C_4$ alkyl radical optionally substituted with a hydroxyl, a ($C_1$-$C_2$)alkoxy, an amino or a (di) ($C_1$-$C_2$) alkylamino;
a phenyl radical.

Preferably, the $R_{11}$ and $R_{12}$ radicals, which may be identical or different, are chosen from a methyl radical, an ethyl radical, a 2-hydroxyethyl radical, a 3-hydroxyethyl radical, a 2-hydroxypropyl radical and a phenyl radical.

According to another embodiment, the $R_{11}$ and $R_{12}$ radicals form, together with the nitrogen atoms to which they are attached, a saturated or unsaturated, optionally substituted, 5- or 6-membered ring.

Preferably, the $R_{11}$ and $R_{12}$ radicals form, together with the nitrogen atoms to which they are attached, a pyrazolidine or pyridazolidine ring, optionally substituted with a $C_1$-$C_4$ alkyl radical, a hydroxyl, a ($C_1$-$C_2$)alkoxy, a carboxyl, a carboxamido, an amino or a (di)($C_1$-$C_2$)alkylamino.

Even more advantageously, the $R_{11}$ and $R_{12}$ radicals form, together with the nitrogen atoms to which they are attached, a pyrazolidine or pyridazolidine ring.

As regards the $R_{13}$ and $R_{14}$ radicals, said radicals, which may be identical or different, are more particularly chosen from a hydrogen atom; a linear or branched $C_1$-$C_4$ alkyl radical optionally substituted with one or more hydroxyl, $(C_1$-$C_2)$alkoxy, amino or (di) $(C_1$-$C_2)$alkylamino; and a phenyl radical optionally substituted with a hydroxyl, amino or $(C_1$-$C_2)$alkoxy radical.

Preferably, the $R_{13}$ and $R_{14}$ radicals, which may be identical or different, are chosen from a hydrogen atom, and a methyl, ethyl, isopropyl, 2-hydroxyethyl, 3-hydroxypropyl, 2-hydroxypropyl and 2-carboxyethyl. According to one particular embodiment, the $R_{13}$ and $R_{14}$ radicals represent a hydrogen atom.

According to another embodiment, the $R_{13}$ and $R_{14}$ radicals form, together with the nitrogen atom to which they are attached, a 5- or 7-membered ring chosen from pyrrolidine, piperidine, homopiperidine, piperazine and homopiperazine heterocycles; it being possible for said rings to be substituted with one or more of the following radicals: hydroxyl, amino, (di)$(C_1$-$C_2)$alkylamino, carboxyl, carboxyamido or $C_1$-$C_4$ alkyl optionally substituted with one or more hydroxyl, amino or $C_1$-$C_2$ (di)alkylamino.

More particularly, the $R_{13}$ and $R_{14}$ radicals form, together with the nitrogen atom to which they are attached, a 5- or 7-membered ring chosen from pyrrolidine, 2,5-dimethylpyrrolidine, pyrrolidine-2-carboxylic acid, 3-hydroxypyrrolidine-2-carboxylic acid, 4-hydroxypyrrolidine-2-carboxylic acid, 2,4-dicarboxypyrrolidine, 3-hydroxy-2-hydroxymethyl-pyrrolidine, 2-carboxamidopyrrolidine, 3-hydroxy-2-carboxamidopyrrolidine, 2-(diethylcarbox-amido)pyrrolidine, 2-(hydroxymethyl)pyrrolidine, 3,4-dihydroxy-2-(hydroxymethyl)pyrrolidine, 3-hydroxy-pyrrolidine, 3,4-dihydroxypyrrolidine, 3-amino-pyrrolidine, 3-methylaminopyrrolidine, 3-dimethylamino-pyrrolidine, 4-amino-3-hydroxypyrrolidine, 3-hydroxy-4-(2-hydroxyethyl)aminopyrrolidine, piperidine, 2,6-di-methylpiperidine, 2-carboxypiperidine, 2-carboxamidopiperidine, 2-hydroxymethylpiperidine, 3-hydroxy-2-hydroxymethylpiperidine, 3-hydroxypiperidine, 4-hydroxypiperidine, 3-hydroxymethylpiperidine, homopiperidine, 2-carboxyhomopiperidine, 2-carboxamido-homopiperidine, homopiperazine, N-methylhomopiperazine, and N-(2-hydroxyethyl)homopiperazine.

Preferably, the $R_{12}$ and $R_{14}$ radicals form, together with the nitrogen atom to which they are attached, a 5- or 7-membered ring chosen from pyrrolidine 3-hydroxy-pyrrolidine, 3-aminopyrrolidine, 3-dimethyl-aminopyrrolidine, pyrrolidine-2-carboxylic acid, 3-hydroxypyrrolidine-2-carboxylic acid, piperidine, hydroxypiperidine, homopiperidine, diazepane, N-methyl-homopiperazine and N-β-hydroxyethylhomopiperazine.

In accordance with an even more preferred embodiment of the invention, the $R_{12}$ and $R_{14}$ radicals form, together with the nitrogen atom to which they are attached, a 5-membered ring such as pyrrolidine, 3-hydroxypyrrolidine, 3-aminopyrrolidine or 3-dimethylaminopyrrolidine.

The compounds of formula (II) can optionally be salified with strong inorganic acids such as, for example, HCl, HBr, HI, $H_2SO_4$ or $H_3PO_4$, or organic acids such as, for example, acetic acid, lactic acid, tartaric acid, citric acid, succinic acid, benzenesulphonic acid, para-toluenesulphonic acid, formic acid and methanesulphonic acid.

They can also be in the form of solvates, for example a hydrate or a solvate of a linear or branched alcohol, such as ethanol or isopropanol.

By way of examples of derivatives of formula (IV), mention may be made of the compounds present below or addition salts thereof:

4,5-diamino-1,2-dimethyl-1,2-dihydropyrazol-3-one.
4-amino-5-methylamino-1,2-dimethyl-1,2-dihydropyrazol-3-one.
4-amino-5-dimethylamino-1,2-dimethyl-1,2-dihydro-pyrazol-3-one.
4-amino-5-(2-hydroxyethyl)amino-1,2-dimethyl-1,2-dihydropyrazol-3-one.
4-amino-5-(pyrrolidin-1-yl)-1,2-dimethyl-1,2-dihydropyrazol-3-one.
4-amino-5-(piperidin-1-yl)-1,2-dimethyl-1,2-dihydropyrazol-3-one.
4,5-diamino-1,2-di(2-hydroxyethyl)-1,2-dihydro-pyrazol-3-one.
4-amino-5-methylamino-1,2-di(2-hydroxyethyl)-1,2-dihydropyrazol-3-one.
4-amino-5-dimethylamino-1,2-di(2-hydroxyethyl)-1,2-dihydropyrazol-3-one.
4-amino-5-(2-hydroxyethyl)amino-1,2-di(2-hydroxyethyl)-1,2-dihydropyrazol-3-one.
4-amino-5-(pyrrolidin-1-yl)-1,2-di(2-hydroxyethyl)-1,2-dihydropyrazol-3-one.
4-amino-5-(piperidin-1-yl)-1,2-di(2-hydroxyethyl)-1,2-dihydropyrazol-3-one.
4,5-diamino-1,2-diethyl-1,2-dihydropyrazol-3-one.
4,5-diamino-1,2-phenyl-1,2-dihydropyrazol-3-one.
4,5-diamino-1-ethyl-2-methyl-1,2-dihydropyrazol-3-one.
4,5-diamino-2-ethyl-1-methyl-1,2-dihydropyrazol-3-one.
4,5-diamino-1-phenyl-2-methyl-1,2-dihydropyrazol-3-one.
4,5-diamino-1-(2-hydroxyethyl)-2-methyl-1,2-dihydropyrazol-3-one.
4,5-diamino-2-(2-hydroxyethyl)-1-methyl-1,2-dihydropyrazol-3-one.
2,3-diamino-6,7-dihydro-1H,5H-pyrazolo[1,2-a]pyrazol-1-one
2-amino-3-methylamino-6,7-dihydro-1H,5H-pyrazolo[1,2-a]pyrazol-1-one
2-amino-3-dimethylamino-6,7-dihydro-1H,5H-pyrazolo[1,2-a]pyrazol-1-one
2-amino-3-ethylamino-6,7-dihydro-1H,5H-pyrazolo[1,2-a]pyrazol-1-one
2-amino-3-isopropylamino-6,7-dihydro-1H,5H-pyrazolo[1,2-a]pyrazol-1-one
2-amino-3-(2-hydroxyethyl)amino-6,7-dihydro-1H,5H-pyrazolo[1,2-a]pyrazol-1-one
2-amino-3-(2-hydroxypropyl)amino-6,7-dihydro-1H,5H-pyrazolo[1,2-a]pyrazol-1-one
2-amino-3-bis(2-hydroxyethyl)amino-6,7-dihydro-1H,5H-pyrazolo[1,2-a]pyrazol-1-one
2-amino-3-(pyrrolidin-1-yl)-6,7-dihydro-1H,5H-pyrazolo[1,2-a]pyrazol-1-one
2-amino-3-(3-hydroxypyrrolidin-1-yl)-6,7-dihydro-1H,5H-pyrazolo[1,2-a]pyrazol-1-one
2-amino-3-(piperidin-1-yl)-6,7-dihydro-1H,5H-pyrazolo[1,2-a]pyrazol-1-one
2,3-diamino-6-hydroxy-6,7-dihydro-1H,5H-pyrazolo[1,2-a]pyrazol-1-one
2,3-diamino-6-methyl-6,7-dihydro-1H,5H-pyrazolo[1,2-a]pyrazol-1-one
2,3-diamino-6-dimethyl-6,7-dihydro-1H,5H-pyrazolo[1,2-a]pyrazol-1-one 2,3-diamino-5,6,7,8-tetrahydro-1H,6H-pyridazino[1,2-a]pyrazol-1-one
2,3-diamino-5,8-dihydro-1H,6H-pyridazino[1,2-a]pyrazol-1-one
4-Amino-5-dimethylamino-1,2-diethyl-1,2-dihydro-pyrazol-3-one
4-Amino-1,2-diethyl-5-ethylamino-1,2-dihydro-pyrazol-3-one
4-Amino-1,2-diethyl-5-isopropylamino-1,2-dihydro-pyrazol-3-one
4-Amino-1,2-diethyl-5-(2-hydroxyethylamino)-1,2-dihydropyrazol-3-one
4-Amino-5-(2-dimethylaminoethylamino)-1,2-diethyl-1,2-dihydropyrazol-3-one
4-Amino-5-[bis(2-hydroxyethyl)amino]-1,2-diethyl-1,2-dihydropyrazol-3-one
4-Amino-1,2-diethyl-5-(3-imidazol-1-yl-propylamino)-1,2-dihydropyrazol-3-one
4-Amino-5-dimethylamino-1,2-diethyl-1,2-dihydro-pyrazol-3-one
4-Amino-1,2-diethyl-5-ethylamino-1,2-dihydro-pyrazol-3-one
4-Amino-1,2-diethyl-5-isopropylamino-1,2-dihydro-pyrazol-3-one
4-Amino-1,2-diethyl-5-(2-hydroxyethylamino)-1,2-dihydropyrazol-3-one
4-Amino-5-(2-dimethylaminoethylamino)-1,2-diethyl-1,2-dihydropyrazol-3-one
4-Amino-5-[bis(2-hydroxyethyl)amino]-1,2-diethyl-1,2-dihydropyrazol-3-one
4-Amino-1,2-diethyl-5-(3-imidazol-1-yl-propylamino)-1,2-dihydropyrazol-3-one
4-Amino-1,2-diethyl-5-(3-hydroxypyrrolidin-1-yl)-1,2-dihydropyrazol-3-one
4-Amino-1,2-diethyl-5-pyrrolidin-1-yl-1,2-dihydro-pyrazol-3-one
4-Amino-5-(3-dimethylaminopyrrolidin-1-yl)-1,2-diethyl-1,2-dihydropyrazol-3-one
4-Amino-1,2-diethyl-5-(4-methylpiperazin-1-yl)-pyrazolidin-3-one
2,3-Diamino-6-hydroxy-6,7-dihydro-5H-pyrazolo[1,2-a]pyrazol-1-one some of which are represented below in order to illustrate the names with chemical structures:

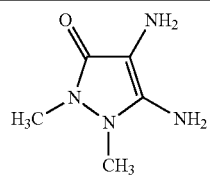 4,5-Diamino-1,2-dimethyl-1,2-dihydropyrazol-3-one

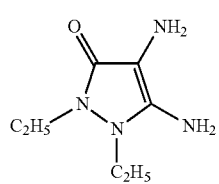 [SMILES: CCn1c(N)c(N)c(=O)n1CC] 4,5-Diamino-1,2-diethyl-1,2-dihydropyrazol-3-one

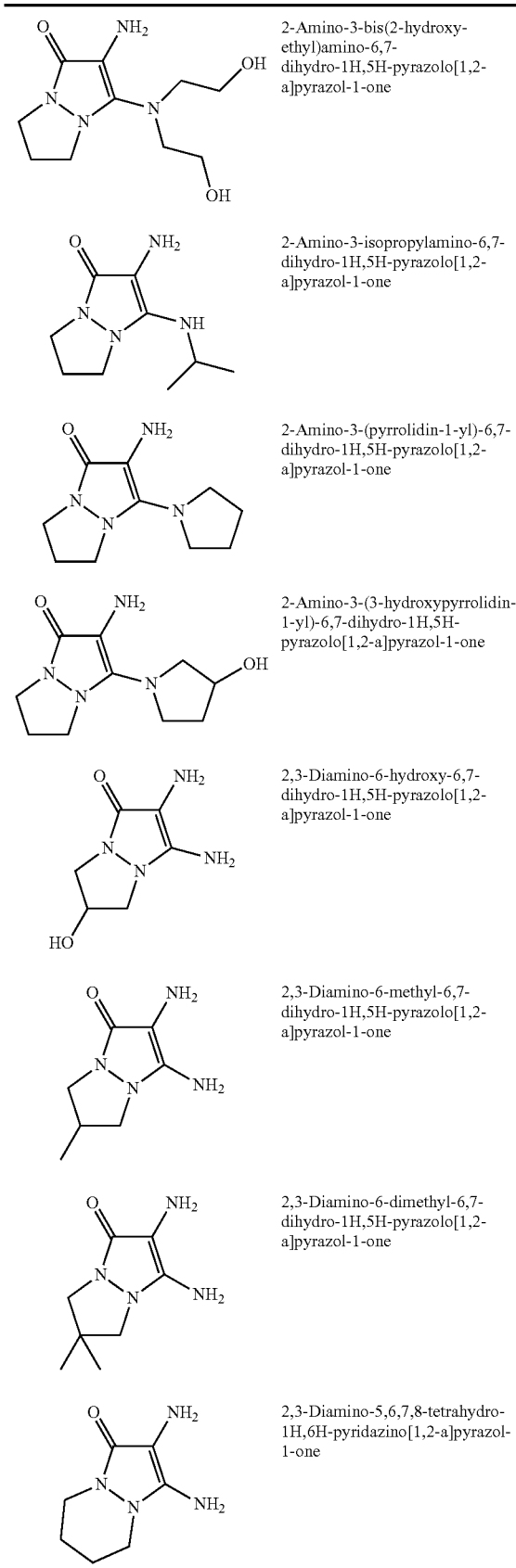

2-Amino-3-bis(2-hydroxyethyl)amino-6,7-dihydro-1H,5H-pyrazolo[1,2-a]pyrazol-1-one 2-Amino-3-isopropylamino-6,7-dihydro-1H,5H-pyrazolo[1,2-a]pyrazol-1-one 2-Amino-3-(pyrrolidin-1-yl)-6,7-dihydro-1H,5H-pyrazolo[1,2-a]pyrazol-1-one 2-Amino-3-(3-hydroxypyrrolidin-1-yl)-6,7-dihydro-1H,5H-pyrazolo[1,2-a]pyrazol-1-one 2,3-Diamino-6-hydroxy-6,7-dihydro-1H,5H-pyrazolo[1,2-a]pyrazol-1-one 2,3-Diamino-6-methyl-6,7-dihydro-1H,5H-pyrazolo[1,2-a]pyrazol-1-one 2,3-Diamino-6-dimethyl-6,7-dihydro-1H,5H-pyrazolo[1,2-a]pyrazol-1-one 2,3-Diamino-5,6,7,8-tetrahydro-1H,6H-pyridazino[1,2-a]pyrazol-1-one

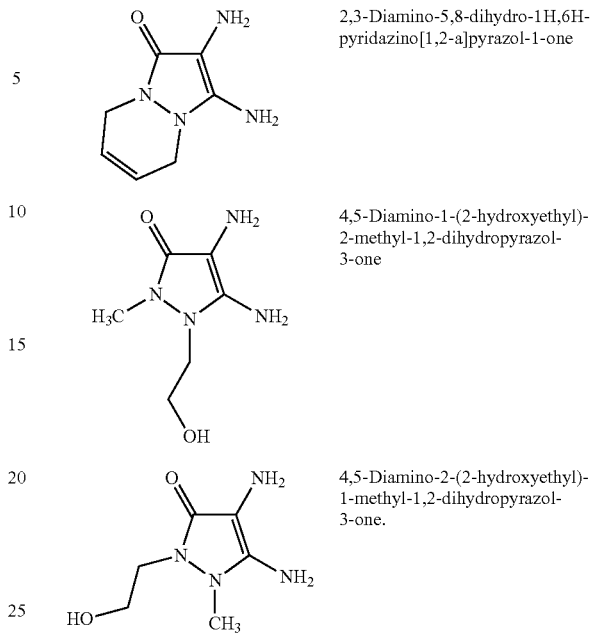

2,3-Diamino-5,8-dihydro-1H,6H-pyridazino[1,2-a]pyrazol-1-one 4,5-Diamino-1-(2-hydroxyethyl)-2-methyl-1,2-dihydropyrazol-3-one 4,5-Diamino-2-(2-hydroxyethyl)-1-methyl-1,2-dihydropyrazol-3-one.

Among these compounds, the diamino-N,N-dihydropyrazolone derivatives of formula (IV) or addition salts thereof which are particularly preferred are:
2,3-Diamino-6,7-dihydro-1H,5H-pyrazolo[1,2-a]pyrazol-1-one
2-Amino-3-ethylamino-6,7-dihydro-1H,5H-pyrazolo[1,2-a]pyrazol-1-one
2-Amino-3-isopropylamino-6,7-dihydro-1H,5H-pyrazolo[1,2-a]pyrazol-1-one
2-Amino-3-(pyrrolidin-1-yl)-6,7-dihydro-1H,5H-pyrazolo[1,2-a]pyrazol-1-one
4,5-Diamino-1,2-dimethyl-1,2-dihydropyrazol-3-one
4,5-Diamino-1,2-diethyl-1,2-dihydropyrazol-3-one
4,5-Diamino-1,2-di-(2-hydroxyethyl)-1,2-dihydro-pyrazol-3-one.
2-Amino-3-(2-hydroxyethyl)amino-6,7-dihydro-1H,5H-pyrazolo[1,2-a]pyrazol-1-one
2-Amino-3-dimethylamino-6,7-dihydro-1H,5H-pyrazolo[1,2-a]pyrazol-1-one
2,3-Diamino-5,6,7,8-tetrahydro-1H,6H-pyridazino[1,2-a]pyrazol-1-one.

According to one embodiment, the oxidation base of formula (II) is 2,3-diamino-6,7-dihydro-1H,5H-pyrazolo[1,2-a]pyrazol-1-one.

According to one variant, the composition of the invention comprises an oxidation base of formula (II) and/or (III) and/or (IV), the indole coupler of formula (I) and a second coupler of formula (V) below:

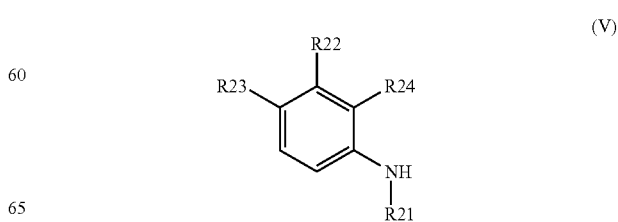

(V)

in which $R_{21}$ represents a hydrogen atom or a $C_1$-$C_4$ hydroxyalkyl radical, $R_{22}$ represents a hydroxyl or amino radical, $R_{23}$ represents a $C_1$-$C_4$ alkyl, $C_1$-$C_4$ hydroxyalkyl, $C_1$-$C_4$ alkoxy or $C_1$-$C_4$ hydroxyalkoxy radical, and $R_{24}$ represents a hydrogen or halogen atom, preferably a hydrogen atom or a chlorine atom.

By way of coupler (V), mention may be made of 2-methyl-5-aminophenol, 5-N-(β-hydroxyethyl)amino-2-methylphenol, 6-chloro-2-methyl-5-aminophenol, 2,4-diaminophenoxyethanol and 1-amino-2-methoxy-5-N-(β-hydroxyethyl)aminobenzene.

Preferably, $R_{22}$ represents a hydroxyl radical and $R_{23}$ represents a $C_1$-$C_4$ alkyl or $C_1$-$C_4$ hydroxyalkyl radical.

The preferred couplers of formula (V) are chosen from 2-methyl-5-aminophenol, 5-N-(β-hydroxyethyl)amino-2-methylphenol and 6-chloro-2-methyl-5-aminophenol.

The composition of the invention preferably comprises an indole coupler of formula (I), a pyrazolopyridine oxidation base chosen from the bases:

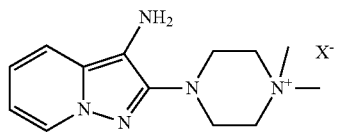

Salt of 4-(3-aminopyrazolo[1,5-a]pyridin-2-yl)-1,1-dimethylpiperazin-1-ium

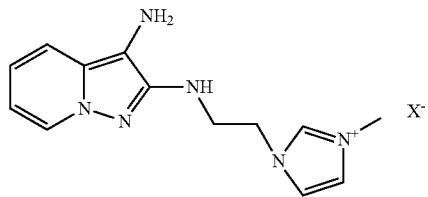

Salt of 3-[2-(3-aminopyrazolo[1,5-a]pyridin-2-ylamino)ethyl]-1-methyl-3H-imidazol-1-ium, and 2-[(3-aminopyrazolo[1,5-a]pyridin-2-yl)oxy]ethanol and its addition salts with an acid, and an additional coupler of formula (V).

According to another variant, the composition of the invention preferably comprises an indole coupler of formula (I), a 2,3-diamino-6,7-dihydro-1H,5H-pyrazolo[1,2-a]pyrazol-1-one oxidation base, and an additional coupler of formula (V).

The compounds of formula (I), (II), (III) or (IV) or (V) are in general each present in an amount of between 0.001% to 10% by weight, approximately, of the total weight of the dye composition, preferably between 0.005% and 6%.

Preferably, the coupler of formula (I)/coupler(s) of formula (V) molar ratio is greater than or equal to 1.

The dye composition according to the invention may contain one or more additional couplers conventionally used for dyeing keratin fibres, other than the couplers of formula (I) or (V) or addition salts thereof with an acid. Among these couplers, mention may in particular be made of meta-phenylenediamines or meta-aminophenols which are different from the compounds of formula (V), meta-diphenols, naphthalene couplers, heterocyclic couplers which are different from the compounds of formula (I), and addition salts thereof.

By way of example of a coupler, mention may be made of 3-aminophenol, 2,4-dichloro-3-aminophenol, 5-amino-4-chloro-o-cresol, 4-chloro-1,3-dihydroxybenzene, 1,3-diaminobenzene, 1,3-bis(2,4-diaminophenoxy)propane, 3-ureidoanilane, 3-ureido-1-dimethylaminobenzene, sesamol, 1-β-hydroxyethylamino-3,4-methylenedioxy-benzene, α-naphthol, 2-methyl-1-naphthol, 1,5-dihydroxynaphthalene, 2,7-naphthalenediol, 1-acetoxy-2-methylnaphthalene, 6-hydroxyindole, 3,5-diamino-2,6-dimethoxypyridine, 2,6-dihydroxy-3-4-dimethylpyridine, 3-amino-2-methylamino-6-methoxypyridine, 1-N-(β-hydroxyethyl)amino-3,4-methylenedioxybenzene, 2,6-bis(β-hydroxyethylamino)toluene, 3-methyl-1-phenyl-5-pyrazolone, 2-amino-3-hydroxypyridine, 1,3-dihydroxybenzene, 1,3-dihydroxy-2-methylbenzene, and addition salts thereof with an acid.

The dye composition of the invention may optionally comprise one or more additional oxidation bases conventionally used for dyeing keratin fibres, which are different from the compound of formula (II) or (III) or (IV).

By way of example, these additional oxidation bases are chosen from para-phenylenediamines, bisphenylalkylenediamines, para-aminophenols, bis-para-aminophenols, ortho-aminophenols, heterocyclic bases which are different from the bases of formula (II) or (III) or (IV) and addition salts thereof.

Among the para-phenylenediamines, mention may be made, by way of example, of para-phenylenediamine, para-toluenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-(β-hydroxyethyl)-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N,N-(ethyl,β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-(β-hydroxyethyloxy)-para-phenylenediamine, 2-(β-acetylaminoethyloxy)-para-phenylenediamine, N-(β-methoxyethyl)-para-phenylenediamine, 2-[{2-[(4-amino-phenyl)amino]ethyl}(2-hydroxyethyl)amino]ethanol, 4-aminophenylpyrrolidine, 2-thienyl-para-phenylene-diamine, 2-(β-hydroxyethylamino)-5-aminotoluene, 3-hydroxy-1-(4'-aminophenyl)pyrrolidine, and addition salts thereof with an acid.

Among the para-phenylenediamines mentioned above, para-phenylenediamine, para-toluenediamine, 2-iso-propyl-para-phenylenediamine, 2-(β-hydroxyethyl)-para-phenylenediamine, 2-(β-hydroxyethyloxy)-para-phenylene-diamine, 2,6-dimethyl-para-phenylenediamine, 2,6-diethyl-para-phenylenediamine, 2,3-dimethyl-para-phenylenediamine, N,N-bis(β-hydroxyethyl)-para-phenylenediamine, 2-chloro-para-phenylenediamine, 2-(β-acetylaminoethyloxy)-para-phenylenediamine, 2-[{2-[(4-aminophenyl)amino]ethyl}(2-hydroxy-ethyl)amino]ethanol and addition salts thereof with an acid are particularly preferred.

Among the bisphenylalkylenediamines mention may be made, by way of example, of N,N'-bis(β-hydroxyethyl)-N, N'-bis(4'-aminophenyl)-1,3-diaminopropanol, N,N'-bis(β-hydroxyethyl)-N,N'-bis(4'-aminophenyl)ethylene-diamine, N,N'-bis(4-aminophenyl)tetramethylenediamine, N,N'-bis (β-hydroxyethyl)-N,N'-bis(4-aminophenyl)tetra-methylenediamine, N,N'-bis(4-methylamino-phenyl)tetramethylenediamine, N,N'-bis(ethyl)-N,N'-bis(4'-amino-3'-methylphenyl)ethylenediamine, 1,8-bis(2,5-diaminophenoxy)-3,6-dioxaoctane, and addition salts thereof with an acid.

Among the para-aminophenols, mention may be made, by way of example, of para-aminophenol, 4-amino-3-methylphenol, 4-amino-3-fluorophenol, 4-amino-3-hydroxymethylphenol, 4-amino-2-methylphenol, 4-amino-2-(hydroxymethyl)phenol, 4-amino-2-(methoxymethyl)phenol, 4-amino-2-(aminomethyl)phenol, 4-amino-2-((β-hydroxyethyl)aminomethyl)phenol, 4-amino-2-fluorophenol, 1-hydroxy-4-(methylamino)benzene, 2,2'-methylenebis(4-aminophenol), and addition salts thereof with an acid.

Among the ortho-aminophenols, mention may be made, by way of example, of 2-aminophenol, 2-amino-5-methylphenol, 2-amino-6-methylphenol, 5-acetamido-2-aminophenol, and addition salts thereof with an acid.

Among the heterocyclic bases, mention may be made, by way of example, of pyridine derivatives, pyrimidine derivatives and pyrazole derivatives.

Among the pyridine derivatives, mention may be made of the compounds described, for example, in patents GB 1 026 978 and GB 1 153 196, such as 2,5-diaminopyridine, 2-(4-methoxyphenyl)amino-3-amino-pyridine, 2,3-diamino-6-methoxypyridine, 2-(β-methoxy-ethyl)amino-3-amino-6-methoxypyridine, 3,4-diaminopyridine, and addition salts thereof with an acid.

Among the pyrimidine derivatives, mention may be made of the compounds described, by way of example, in patents DE 2359399; JP 88-169571; JP 05-63124; EP 0770375 or patent application WO 96/15765, such as 2,4,5,6-tetraminopyrimidine, 4-hydroxy-2,5,6-triaminopyrimidine, 2-hydroxy-4,5,6-triaminopyrimidine, 2,4-dihydroxy-5,6-diaminopyridimine, or 2,5,6-triaminopyrimidine, and pyrazolopyrimidine derivatives, such as those mentioned in patent application FR-A-2750048 and among which mention may be made of pyrazolo[1,5-a]pyrimidine-3,7-diamine; 2,5-dimethyl-pyrazolo[1,5-a]pyrimidine-3,7-diamine; pyrazolo[1,5-a]pyrimidine-3,5-diamine; 2,7-dimethylpyrazolo[1,5-a]pyrimidine-3,5-diamine; 3-aminopyrazolo[1,5-a]pyrimidin-7-ol; 3-aminopyrazolo[1,5-a]pyrimidin-5-ol; 2-(3-aminopyrazolo[1,5-a]pyrimidin-7-ylamino)ethanol, 2-(7-aminopyrazolo[1,5-a]pyrimidin-3-ylamino)ethanol, 2-[(3-aminopyrazolo[1,5-a]pyrimidin-7-yl)(2-hydroxy-ethyl)amino]ethanol, 2-[(7-aminopyrazolo[1,5-a]pyrimidin-3-yl)(2-hydroxyethyl)amino]ethanol, 5,6-di-methylpyrazolo[1,5-a]pyrimidine-3,7-diamine, 2,6-di-methylpyrazolo[1,5-a]pyrimidine-3,7-diamine, 2,5,N7,N7-tetramethylpyrazolo[1,5-a]pyrimidine-3,7-diamine, 3-amino-5-methyl-7-(imidazolylpropylamino)pyrazolo[1,5-a]pyrimidine, and addition salts thereof with an acid and the tautomeric forms thereof, when a tautomeric equilibrium exists.

By way of examples of diaminopyrazole bases, mention may be made of the compounds described in patents DE-A-38 43 892 and DE-A-41 33 957 and patent applications WO 94/08969, WO 94/08970, FR-A-2 733 749 and DE-A-195 43 988, such as 4,5-diamino-1-methylpyrazole, 4,5-diamino-1-(2-hydroxyethyl)pyrazole, 4,5-diamino-1-(4'-chlorobenzyl)pyrazole, 4,5-diamino-1,3-dimethylpyrazole, 4,5-diamino-3-methyl-1-phenyl-pyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-(tert-butyl)-1-methylpyrazole, 4,5-diamino-1-(tert-butyl)-3-methylpyrazole, 4,5-diamino-1(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-(hydroxymethyl)pyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, and addition salts thereof with an acid.

According to one preferred embodiment, the composition comprises the additional oxidation base below or addition salts thereof with an acid:

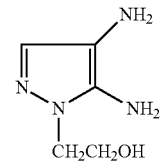

Generally, the addition salts of the additional oxidation bases and of the additional couplers that can be used in the context of the invention are in particular chosen from the addition salts with an acid, such as hydrochlorides, hydrobromides, sulphates, citrates, succinates, tartrates, lactates, tosylates, benzenesulphonates, phosphates and acetates, and the addition salts with a base, such as sodium hydroxide, potassium hydroxide, aqueous ammonia, amines or alkanolamines.

The dye composition in accordance with the invention may also contain one or more direct dyes which can in particular be chosen from nitrobenzene dyes, azo direct dyes or methine direct dyes. These direct dyes can be nonionic, anionic or cationic in nature.

The medium suitable for dyeing, also referred to as dyeing vehicle, generally comprises water or a mixture of water and one or more solvents, for instance $C_1$-$C_4$ lower alkanols, such as ethanol and isopropanol, polyols, for instance propylene glycol, dipropylene glycol or glycerol, and polyol ethers, for instance dipropylene glycol monomethyl ether.

The solvent(s) is (are) generally present in proportions which can be between 1% and 40% by weight, approximately, relative to the total weight of the dye composition, and even more preferably between 3% and 30% by weight, approximately.

The dye composition in accordance with the invention may also contain various adjuvants conventionally used in compositions for dyeing the hair, such as anionic, cationic, nonionic, amphoteric or zwitterionic surfactants or mixtures thereof, anionic, cationic, nonionic, amphoteric or zwitterionic polymers or blends thereof, inorganic or organic thickeners, and in particular anionic, cationic, nonionic and amphoteric polymeric associative thickeners, antioxidants, penetration agents, sequestering agents, fragrances, buffers, dispersing agents, conditioning agents, such as, for example, volatile or non-volatile and modified or unmodified silicones, film-forming agents, ceramides, preservatives or opacifiers.

The above adjuvants are generally present in an amount, for each of them, of between 0.01% and 20% by weight, relative to the weight of the composition.

Of course, those skilled in the art will take care to select this or these optional additional compound(s) in such a way that the advantageous properties intrinsically associated with the oxidation dyeing composition in accordance with the invention are not, or not substantially, impaired by the addition(s) envisaged.

The pH of the dye composition in accordance with the invention is generally between 3 and 12, approximately, and preferably between 5 and 11, approximately. It can be adjusted to the desired value using acidifying or basifying agents commonly used in the dyeing of the keratin fibres, or else by means of conventional buffer systems.

Among the acidifying agents, mention may be made, by way of example, of inorganic or organic acids, such as hydrochloric acid, orthophosphoric acid or sulphuric acid, carboxylic acids such as acetic acid, tartaric acid, citric acid or lactic acid, and sulphonic acids.

Among the basifying agents, mention may be made, by way of example, of aqueous ammonia, alkaline carbonates, alkanolamines, such as mono-, di- and triethanolamines and derivatives thereof, sodium hydroxide, potassium hydroxide and the compounds of formula (V) below:

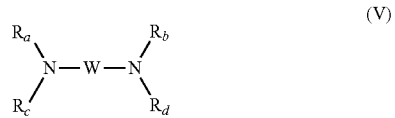

(V)

in which W is a propylene residue optionally substituted with a hydroxyl group or a $C_1$-$C_4$ alkyl radical; and $R_a$, $R_b$, $R_c$ and $R_d$, which may be identical or different, represent a hydrogen atom or a $C_1$-$C_4$ alkyl or $C_1$-$C_4$ hydroxyalkyl radical.

The composition according to the invention may comprise one or more oxidizing agents.

The oxidizing agents are those conventionally used for the oxidation dyeing of keratin fibres and are, for example, hydrogen peroxide, urea peroxide, alkali metal bromates, persalts such as perborates and persulphates, peracids and oxidase enzymes, among which mention may be made of peroxidases, 2-electron oxidoreductases, such as uricases, and 4-electron oxygenases such as laccases. Hydrogen peroxide is particularly preferred.

The composition with or without oxidizing agent according to the invention may be in various forms, such as in the form of liquids, creams or gels, or any other form suitable for carrying out dyeing of keratin fibres, and in particular of human hair.

It can result from the mixing of several compositions at the time of use.

In one particular variant, it results from the mixing of two compositions, one comprising one or more oxidation bases chosen from the compounds of formula (I) or (II) or addition salts thereof with an acid, and one or more couplers chosen from the compounds of formula (I) or addition salts thereof with an acid, another composition comprising one or more oxidizing agents as described above.

The composition of the invention is therefore applied to the hair for colouring of the keratin fibres in the presence of one or more oxidizing agents for colouring the keratin fibres.

The process of the present invention is a process in which the oxidant-free dye composition is applied to the fibres in the presence of an oxidizing agent for a period of time sufficient to develop the desired colouring. The colour can be revealed at acidic, neutral or alkaline pH and the oxidizing agent can be added to the composition of the invention just at the time of use or it can be employed using an oxidizing composition containing it, applied simultaneously with or sequentially to the composition of the invention.

According to one particular embodiment, the oxidant-free composition according to the present invention is mixed, preferably at the time of use, with a composition containing, in a medium suitable for dyeing, one or more oxidizing agents. The mixture obtained is then applied to the keratin fibres. After a leave-in time of 3 to 50 minutes approximately, preferably 5 to 30 minutes approximately, the keratin fibres are rinsed, optionally washed with shampoo, rinsed again, and then dried.

The oxidizing agents are those described above.

The oxidizing composition may also contain various adjuvants conventionally used in compositions for dyeing the hair and as defined above.

The pH of the oxidizing composition containing the oxidizing agent is such that, after mixing with the dye composition, the pH of the resulting composition applied to the keratin fibres preferably ranges between and 12, approximately, and even more preferably between 5 and 11. It can be adjusted to the desired value by means of acidifying or basifying agents customarily used in the dyeing of keratin fibres and as defined above.

A subject of the invention is also a multicompartment dyeing device or dyeing "kit" in which a first compartment contains a composition comprising one or more oxidation bases chosen from the compounds of formula (II) or (III) or (IV) and one or more couplers of formula (I), and a second compartment contains a composition comprising one or more oxidizing agents.

These devices can be provided with a means for delivering the desired mixture onto the hair, such as the devices described in patent FR-2 586 913 in the name of the applicant.

The examples which follow serve to illustrate the invention without, however, being limiting in nature.

EXAMPLES

Compositions C1 to C6 comprise the following ingredients:

|  | C1 | C2 | C2 | C4 | C3 | C6 |
|---|---|---|---|---|---|---|
| : 1-(2-hydroxy-ethyl)-1H-indol-4-ol (compound I) | 0.007 mol. | 0.01 mol | 0.008 mol. | 0.009 mol | 0.0085 mol. | 0.012 mol. |
| 4-(3-Aminopyrazolo[1,5-a]pyridin-2-yl)-1,1-dimethylpiperazin-1-ium chloride hydrochloride (compound (III)) | 0.01 mol. | 0.01 mol |  | 0.009 mol |  | 0.012 mol. |
| 2-Methyl-5-(2-hydroxyethyl)-aminophenol (compound (IV)) | 0.003 mol. |  |  |  |  |  |
| 1-{2-[(3-aminopyrazolo[1,5-a]pyridin-2-yl)amino]ethyl}-3-methyl-1H-imidazol-3-ium chloride hydrochloride (compound (III)) |  |  |  | 0.009 mol. |  |  |
| 2,4-Diaminophenoxy-ethanol dihydrochloride |  |  |  | 0.001 mol. |  |  |

-continued

| | C1 | C2 | C2 | C4 | C3 | C6 |
|---|---|---|---|---|---|---|
| (compound (IV)) 2-[(3-Aminopyrazolo[1,5-a]pyridin-2-yl)oxy]ethanol hydrochloride (compound(II)) | | | | | 0.012 mol. | |
| 6-Chloro-2-methyl-5-aminophenol (compound (IV)) | | | | | 0.0035 mol. | |
| Polyglycerolated oleyl alcohol comprising 2 mol of glycerol | 4 g A.M | 4 g A.M | 4 g A.M | 4 g A.M | 4 g A.M | 4 g A.M |
| Polyglycerolated oleyl alcohol comprising 4 mol of glycerol (78% A.M) | 6 g A.M | 6 g A.M | 6 g A.M | 6 g A.M | 6 g A.M | 6 g A.M |
| Oleic acid | 3 g | 3 g | 3 g | 3 g | 3 g | 3 g |
| Oleyl amine containing 2 mol EO sold under the name ETHOMEEN 012 by the company AKZO | 7 g A.M | 7 g A.M | 7 g A.M | 7 g A.M | 7 g A.M | 7 g A.M |
| Diethylaminopropyl laurylamino succinamate, sodium salt containing 55% A.M | 3 g A.M | 3 g A.M | 3 g A.M | 3 g A.M | 3 g A.M | 3 g A.M |
| Oleyl alcohol | 5 g | 5 g | 5 g | 5 g | 5 g | 5 g |
| Alkyl (C13/C15 70/30, 50% linear) ether carboxylic acid monoethanolamide (2 EO) | 10 g A.M | 10 g A.M | 10 g A.M | 10 g A.M | 10 g A.M | 10 g A.M |
| Propylene glycol | 9.5 g | 9.5 g | 9.5 g | 9.5 g | 9.5 g | 9.5 g |
| Ethyl alcohol | 5 g | 5 g | 5 g | 5 g | 5 g | 5 g |
| Hexylene glycol | 9.3 g | 9.3 g | 9.3 g | 9.3 g | 9.3 g | 9.3 g |
| Sodium metabisulphite in aqueous solution containing 35% A.M | 0.455 g A.M | 0.455 g A.M | 0.455 g A.M | 0.455 g A.M | 0.455 g A.M | 0.455 g A.M |
| Ammonium acetate | 0.8 g | 0.8 g | 0.8 g | 0.8 g | 0.8 g | 0.8 g |
| Antioxidant, sequestering agent | q.s | q.s | q.s | q.s | q.s | q.s |
| Fragrance, preservative | q.s | q.s | q.s | q.s | q.s | q.s |
| Aqueous ammonia containing 20% NH3 | 10.2 g | 10.2 g | 10.2 g | 10.2 g | 10.2 g | 10.2 g |
| Demineralized water | q.s. 100 g | q.s. 100 g | q.s. 100 g | q.s. 100 g | q.s. 100 g | q.s. 100 g |

A.M: Active Material

Method of Application

Each composition was diluted extemporaneously with 1 times its weight of 20-volume aqueous hydrogen peroxide solution.

Each of the mixtures was applied to grey hair containing 90% white hairs in a proportion of 10 g of mixture per 1 g of hair. After a leave-in period of 30 min at ambient temperature, the hair was then rinsed, washed with a standard shampoo and dried.

Results

The hair colouring was evaluated visually.

The two compositions C1 and C2 result in a blonde shade with a blue tint.

The two compositions C2 and C4 result in a chestnut-brown shade with a deep blue tint.

The two compositions C5 and C6 result in a light chestnut-brown shade with an iridescent dark purple tint.

The colourings obtained with the combinations of the dyes of the invention are particularly chromatic.

Dyeing Examples

Compositions C1 and C2 comprise the following ingredients (mol %):

| | C1 | C2 |
|---|---|---|
| 1-(2-hydroxyethyl)-1H-indol-4-ol (compound I) | 0.008 mol | 0.008 mol |
| 2,3-Diamino-6,7-dihydro-1H,5H-pyrazolo[1,2-a]pyrazol-1-one dimethanesulphonate(compound II) | 0.008 mol | 0.01 mol |
| 6-Chloro-2-methyl-5-aminophenol | — | 0.002 mol |
| Polyglycerolated oleyl alcohol comprising 2 mol of glycerol | 4 g A.M | 4 g A.M |
| Polyglycerolated oleyl alcohol comprising 4 mol of glycerol (78% A.M) | 6 g A.M | 6 g A.M |
| Oleic acid | 3 g | 3 g |
| Oleyl amine 2 mol EO marketed under the name ETHOMEEN 012 by the company AKZO | 7 g A.M | 7 g A.M |
| Diethylaminopropyl laurylamino succinamate, sodium salt containing 55% A.M | 3 g A.M | 3 g A.M |
| Oleyl alcohol | 5 g | 5 g |
| Alkyl (C13/C15 70/30, 50% linear) ether carboxylic acid monoethanolamide (2 EO) | 10 g A.M | 10 g A.M |
| Propylene glycol | 9.5 g | 9.5 g |
| Ethyl alcohol | 5 g | 5 g |
| Hexylene glycol | 9.3 g | 9.3 g |
| Sodium metabisulphite in aqueous solution containing 35% A.M | 0.455 g A.M | 0.455 g A.M |
| Ammonium acetate | 0.8 g | 0.8 g |
| Antioxidant, sequestering agent | q.s | q.s |
| Fragrance, preservative | q.s | q.s |
| Aqueous ammonia containing 20% NH3 | 10.2 g | 10.2 g |
| Demineralized water | q.s 100 g | q.s 100 g |

A.M: Active Material

Method of Application

Each composition was diluted extemporaneously with one times its weight of 20-volume aqueous hydrogen peroxide solution.

Each of the mixtures was applied to grey hair containing 90% white hairs in a proportion of 10 g of mixture per 1 g of hair. After a leave-in time of 30 min at ambient temperature, the hair was rinsed, washed with a standard shampoo and dried.

Results

The hair colouring was evaluated visually.

The two compositions C1 and C2 result in a blonde shade with a coppery tint.

The colourings obtained with the combinations of dyes of the invention are particularly chromatic.

The invention claimed is:

1. Dye composition for keratin fibres, comprising, in a suitable dyeing medium,
a coupler of formula (I) or addition salts thereof with an acid

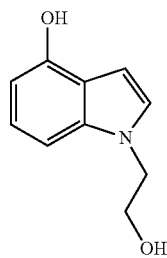
(I)

one or more heterocyclic oxidation bases chosen from the aminopyrazolopyridine bases of formula (II) or (III) and the diamino-N,N-dihydropyrazolone bases of formula (IV),

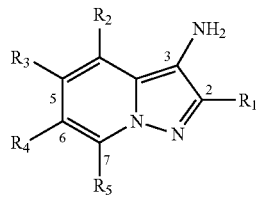
(II)

in which:
R$_1$, R$_2$, R$_3$, R$_4$ and R$_5$, which may be identical or different, represent a hydrogen or halogen atom; an —NHSO$_3$H radical; a hydroxyl radical; a (C$_1$-C$_4$) alkyl radical; a (C$_1$-C$_4$) alkoxy radical; a (C$_1$-C$_4$) alkylthioradical; mono (C$_1$-C$_4$) alkylamino; a di (C$_1$-C$_4$) alkylamino radical in which the two alkyl groups can, together with the nitrogen atom to which they are attached, form a ring which can be interrupted with one or more nitrogen, oxygen or sulphur atoms; a heterocycle; a nitro radical; a phenyl radical; a carbonyl radical; a (C$_1$-C$_4$) alkoxycarbonyl radical; a carboxamido radical; a cyano radical; an amino radical; a sulphonyl radical; a —CO$_2$H radical, an —SO$_3$H radical; a —PO$_3$H$_2$ radical; a —PO$_4$H$_2$ radical; or a group:

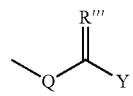

in which R''' represents an oxygen or nitrogen atom, Q represents an oxygen atom, an NH group or an NH(C$_1$-C$_4$) alkyl group, and Y represents a hydroxyl, amino, C$_1$-C$_4$ alkyl, (C$_1$-C$_4$) alkoxy, (C$_1$-C$_4$) alkylamino, or di(C$_1$-C$_4$) alkylamino radical; or

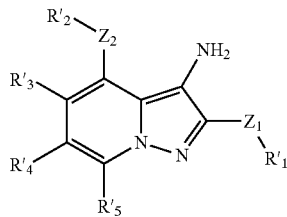
(III)

in which:
Z$_1$ and Z$_2$ independently represent
a single covalent bond,
a divalent radical chosen from:
an —O(CH$_2$)$_p$— radical, p denoting an integer ranging from 0 to 6,
an —NR'$_6$(CH$_2$)$_q$(C$_6$H$_4$)$_t$— radical, q denoting an integer ranging from 0 to 6 and t denoting 0 or 1. R'$_6$ represents a hydrogen atom or a C$_1$-C$_6$ alkyl radical optionally substituted with one or more hydroxyl groups,
Z$_1$ can also represent a divalent radical —S—, —SO— or —SO$_2$— when R'$_1$, is a methyl radical,
R'$_1$, and R'$_2$ represent independently:
a hydrogen,
a C$_1$-C$_{10}$ alkyl radical, which is optionally substituted and optionally interrupted with a heteroatom or a group chosen from O, N, Si, S, SO and SO$_2$,
a halogen,
an SO$_3$H radical,
a saturated, unsaturated or aromatic, substituted or unsubstituted, 5- to 8-membered ring optionally containing one or more heteroatoms or groups chosen from N, O, S, SO$_2$ and —CO—, it being possible for the ring to be cationic and/or substituted with a cationic radical,
an —N$^+$R$_{17}$R$_{18}$R$_{19}$ group, R$_{17}$, R$_{18}$, and R$_{19}$ being linear or branched
C$_1$-C$_5$ alkyls optionally substituted with one or more hydroxyl groups, when Z$_1$ or Z$_2$ represents a covalent bond, then R'$_1$, or R'$_2$ can also represent one of the following radicals:
optionally substituted C$_1$-C$_6$ alkylcarbonyl,
—O—CO—R, —CO—O—R, NR—CO—R' or —CO—NRR' in which R and R' independently represent a hydrogen atom or an optionally substituted C$_1$-C$_6$ alkyl radical,
R'$_3$, R'$_4$ and R'$_5$, which may be identical or different, represent:
a hydrogen atom,
a hydroxyl radical,
a C$_1$-C$_6$ alkoxy radical,
a C$_1$-C$_6$ alkylthio radical,
an amino radical,
a monoalkylamino radical,
a C$_1$-C$_6$ dialkylamino radical in which the alkyl radicals can form, with the nitrogen atom to which they are attached, a saturated or unsaturated and aromatic or non-aromatic 5- to 8-membered heterocycle which can contain one or more heteroatoms or groups chosen from N, O, S, SO$_2$ and CO, it being possible for the hetrocycle to be cationic and/or substituted with a cationic radical, an optionally substituted $C_1$-$C_6$ alkylcarbonyl radical,
an —O—CO—R, —CO—O—R, NR—CO—R' or —CO—NRR' radical with R and R' as defined above,
a halogen,
an —NHSO$_3$H radical,
an optionally substituted $C_1$-$C_4$ alkyl radical,
a saturated, unsaturated or aromatic and optionally substituted carbon ring,
it being possible for R'$_3$, R'$_4$ and R'$_5$ to form, in pairs, a saturated or unsaturated ring, X represents an ion or a group of ions which makes it possible to provide the electronegativity of the derivative of formula (II), with the condition that at least one of the groups R'$_1$, and R'$_2$ represents a cationic radical,

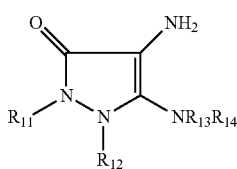

(IV)

in which:

$R_{11}$, $R_{12}$, $R_{13}$ and $R_{14}$, which may be identical or different, represent:
a linear or branched $C_1$-$C_6$ alkyl radical optionally substituted with one or more radicals chosen from the group constituted of an OR$_{15}$ radical, an NR$_6$R$_7$ radical, a carboxyl radical, a sulphonic radical, a carboxamido radical CONR$_{16}$R$_{17}$, a sulphonamido radical SO$_2$NR$_{16}$R$_{17}$, a heteroaryl, an aryl optionally substituted with a ($C_1$-$C_4$) alkyl group, a hydroxyl, a $C_1$-$C_2$ alkoxy, an amino, a (di) ($C_1$-$C_2$) alkylamino;
an aryl radical optionally substituted with one or more ($C_1$-$C_4$) alkyl, hydroxyl, $C_1$-$C_2$ alkoxy, amino, (di) ($C_1$-$C_2$) alkylamino;
a 5- or 6-membered heteroaryl radical optionally substituted with one or more radicals chosen from ($C_1$-$C_4$) alkyl and ($C_1$-$C_2$) alkoxy;

$R_{13}$ and $R_{14}$ can also represent a hydrogen atom;

$R_{15}$, $R_{16}$ and $R_{17}$, which may be identical or different, represent a hydrogen atom; a linear or branched $C_1$-$C_4$ alkyl radical optionally substituted with one or more radicals chosen from the group constituted of a hydroxyl, a $C_1$-$C_2$ alkoxy, a carboxamido CONR$_{18}$R$_{19}$, a sulphonyl SO$_2$R$_{18}$, an aryl optionally substituted with a ($C_1$-$C_4$) alkyl, a hydroxyl, a $C_1$-$C_2$ alkoxy, an amino, a (di) ($C_1$-$C_2$) alkylamino; an aryl optionally substituted with a ($C_1$-$C_4$) alkyl, a hydroxyl, a $C_1$-$C_2$ alkoxy, an amino, a (di) ($C_1$-$C_2$) alkylamino;

$R_{16}$ and $R_{17}$, which may be identical or different, can also represent a carboxamido radical CONR$_{18}$R$_{19}$; a sulphonyl SO$_2$R$_{18}$;

$R_{18}$ and $R_{19}$, which may be identical or different, represent a hydrogen atom; a linear or branched $C_1$-$C_4$ alkyl radical optionally substituted with one or more hydroxyl or $C_1$-$C_2$ alkoxy;

$R_{11}$ and $R_{12}$, on the one hand, and $R_{13}$ and $R_{14}$, on the other hand, can form, with the nitrogen atoms to which they are attached, a saturated or unsaturated heterocycle comprising 5 to 7 ring members, optionally substituted with one or more radicals chosen from the group constituted of halogen atoms, amino, (di) ($C_1$-$C_4$) alkylamino, hydroxyl, carboxyl, carboxamido and ($C_1$-$C_2$) alkoxy radicals, and $C_1$-$C_4$ alkyl radicals optionally substituted with one or more hydroxyl, amino, (di) alkylamino, alkoxy, carboxyl, or sulphonyl radicals;

$R_{13}$ and $R_{14}$ can also form, together with the nitrogen atom to which they are attached, a 5- or 7-membered heterocycle, the carbon atoms of which can be replaced with an optionally substituted oxygen or nitrogen atom.

\* \* \* \* \*